United States Patent
Ebata

(10) Patent No.: US 10,402,960 B2
(45) Date of Patent: Sep. 3, 2019

(54) DRUG VERIFICATION DEVICE, DRUG VERIFICATION SYSTEM AND DRUG VERIFICATION METHOD

(71) Applicant: FUJIFILM Corporation, Tokyo (JP)

(72) Inventor: Tetsuro Ebata, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 91 days.

(21) Appl. No.: 15/066,217

(22) Filed: Mar. 10, 2016

(65) Prior Publication Data

US 2016/0203291 A1    Jul. 14, 2016

Related U.S. Application Data

(63) Continuation of application No. PCT/JP2014/074814, filed on Sep. 19, 2014.

(30) Foreign Application Priority Data

Sep. 26, 2013   (JP) .................................. 2013-199867

(51) Int. Cl.
    *A61J 3/00*     (2006.01)
    *A61J 7/02*     (2006.01)
    (Continued)

(52) U.S. Cl.
    CPC ................ *G06T 7/001* (2013.01); *A61J 7/02* (2013.01); *G06F 19/3462* (2013.01); *G06K 9/00* (2013.01); *A61J 3/007* (2013.01)

(58) Field of Classification Search
    None
    See application file for complete search history.

(56) References Cited

U.S. PATENT DOCUMENTS

| 6,031,942 A * | 2/2000 | Nakayama | G06K 9/00087 382/124 |
| 6,707,934 B1 * | 3/2004 | Takeda | G06K 9/00087 356/71 |

(Continued)

FOREIGN PATENT DOCUMENTS

| JP | 05-337168 A | 12/1993 |
| JP | 2005-034479 A | 2/2005 |

(Continued)

OTHER PUBLICATIONS

JP02005056252A Yoshino et al (computer generated english translation Aug. 6, 2003.*

(Continued)

*Primary Examiner* — Nancy Bitar
(74) *Attorney, Agent, or Firm* — Sughrue Mion, PLLC

(57) ABSTRACT

A drug collation device 10 includes a registered image acquisition unit 12 that acquires an image of a drug as a registered image on the basis of prescription information 22, a collation image acquisition unit 14 that acquires an image of a drug to be collated as a collation image, a similarity calculation unit 16 that calculates similarities between partial images in each corresponding divided region among a plurality of divided regions of the registered image acquired by the registered image acquisition unit 12 and a plurality of divided regions of the collation image acquired by the collation image acquisition unit 14, and a determination unit 18 that determines whether the drug indicated by the registered image and the drug indicated by the collation image are the same type, on the basis of the lowest similarity among a plurality of similarities calculated by the similarity calculation unit 16.

19 Claims, 13 Drawing Sheets

(51) Int. Cl.
    *G06T 7/00*     (2017.01)
    *G06F 19/00*     (2018.01)
    *G06K 9/00*     (2006.01)

(56) References Cited

U.S. PATENT DOCUMENTS

| | | | | |
|---|---|---|---|---|
| 7,512,275 | B2* | 3/2009 | Yumoto | G06K 9/00087 |
| | | | | 382/224 |
| 10,217,010 | B2* | 2/2019 | Shiiyama | G06K 9/00295 |
| 10,217,012 | B2* | 2/2019 | Hasegawa | G01N 21/85 |
| 2003/0021480 | A1* | 1/2003 | Ishitsu | G06T 7/00 |
| | | | | 382/204 |
| 2005/0084155 | A1* | 4/2005 | Yumoto | G06K 9/00087 |
| | | | | 382/190 |
| 2008/0317349 | A1* | 12/2008 | Ishikawa | G06K 9/00221 |
| | | | | 382/190 |
| 2013/0342676 | A1 | 12/2013 | Amano et al. | |
| 2017/0039419 | A1* | 2/2017 | Shiiyama | G06K 9/00926 |

FOREIGN PATENT DOCUMENTS

| | | |
|---|---|---|
| JP | 2005-056252 A | 3/2005 |
| JP | 2010-117331 A | 5/2010 |
| JP | 2013-066533 A | 4/2013 |
| JP | 2013-144101 A | 7/2013 |
| WO | 2004/112685 A1 | 12/2004 |

OTHER PUBLICATIONS

English translation for JP 2005056252;Yoshino et al Mar. 2005.*
International Search Report for PCT/JP2014/074814 dated Nov. 18, 2014 [PCT/ISA/210].
Written Opinion for PCT/JP2014/074814 dated Nov. 18, 2014 [PCT/ISA/237].

* cited by examiner

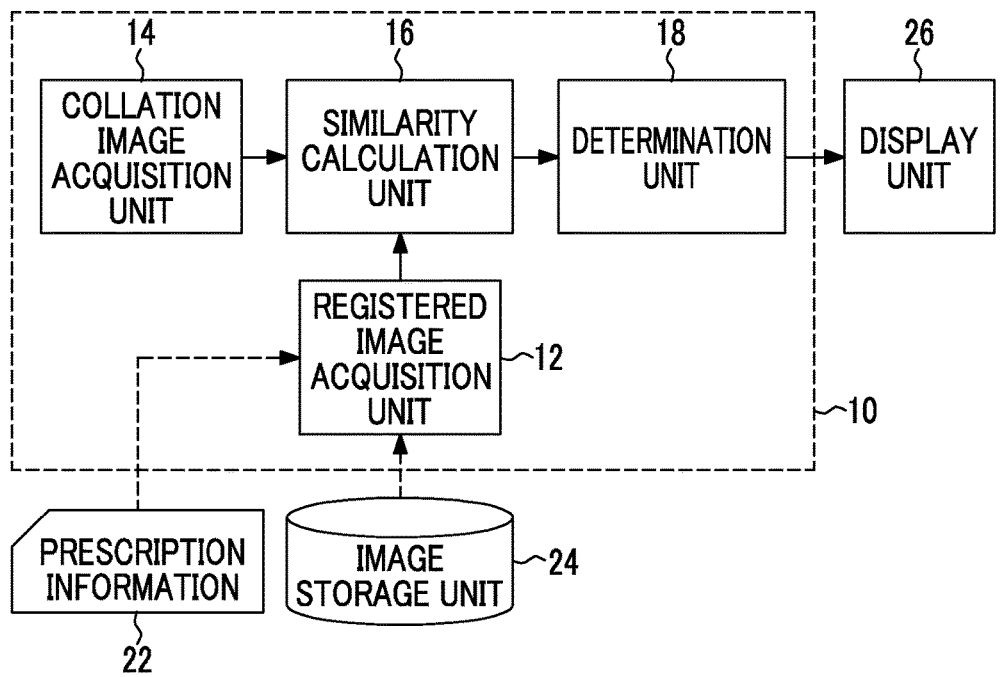
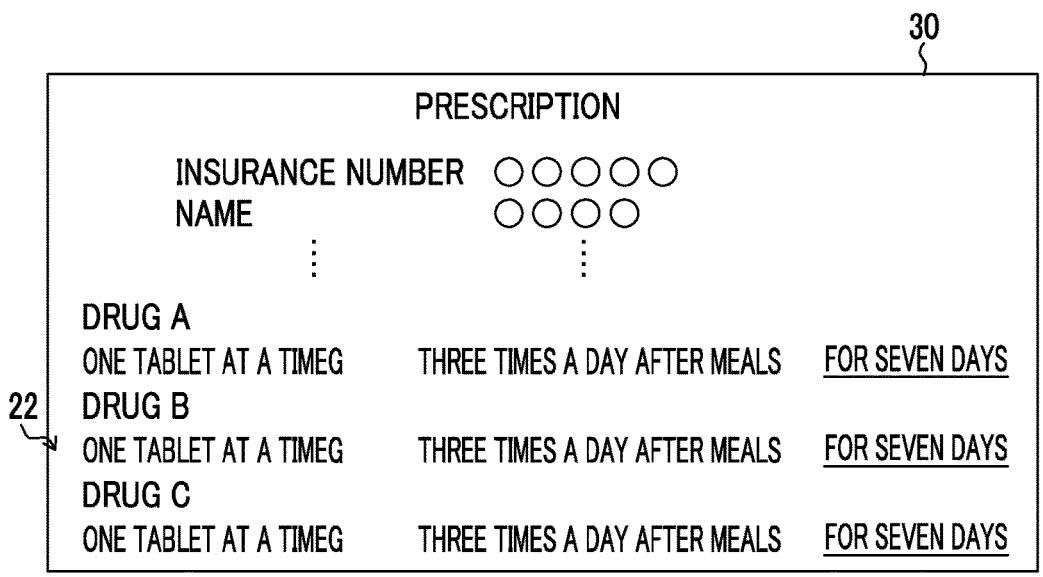

FIG. 6C
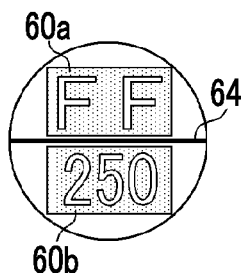
FIG. 7
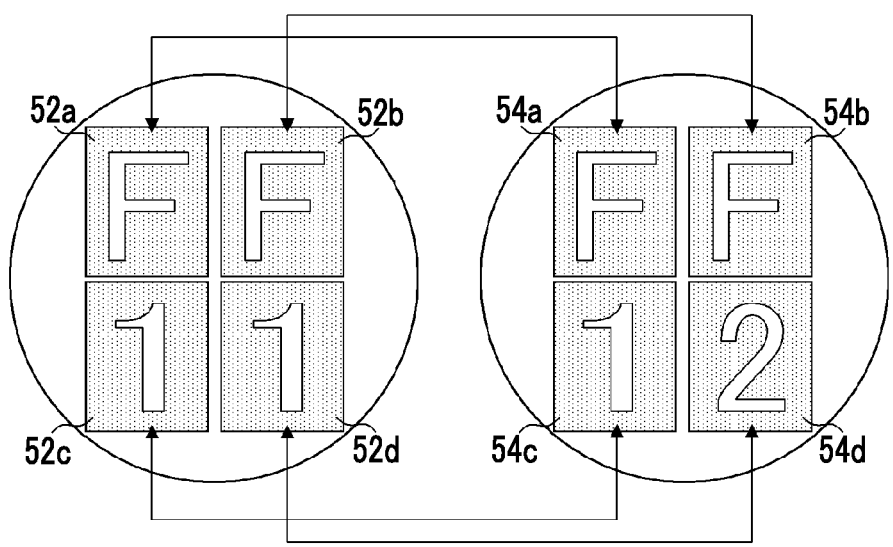
FIG. 8
| POSITION | UPPER LEFT | UPPER RIGHT | LOWER LEFT | LOWER RIGHT |
|---|---|---|---|---|
| SIMILARITY | 0.95 | 0.93 | 0.91 | 0.52 |

FIG. 10

| POSITION | UPPER LEFT | UPPER RIGHT | LOWER LEFT | LOWER RIGHT |
|---|---|---|---|---|
| FIRST SIMILARITY | 0.95 | 0.93 | 0.91 | 0.52 |
| SECOND SIMILARITY | 0.91 | 0.89 | 0.94 | 0.60 |
| THIRD SIMILARITY | 0.90 | 0.90 | 0.93 | 0.55 |
| REPRESENTATIVE SIMILARITY IN EACH FIELD | 0.95 | 0.93 | 0.94 | 0.60 |

FIG. 11

| POSITION | UPPER LEFT | UPPER RIGHT | LOWER LEFT | LOWER RIGHT |
|---|---|---|---|---|
| FIRST SIMILARITY | 0.94 | 0.92 | 0.55 | 0.90 |
| SECOND SIMILARITY | 0.93 | 0.92 | 0.95 | 0.94 |
| THIRD SIMILARITY | 0.94 | 0.95 | 0.96 | 0.93 |
| REPRESENTATIVE SIMILARITY IN EACH FIELD | 0.94 | 0.95 | 0.96 | 0.94 |

FIG. 13

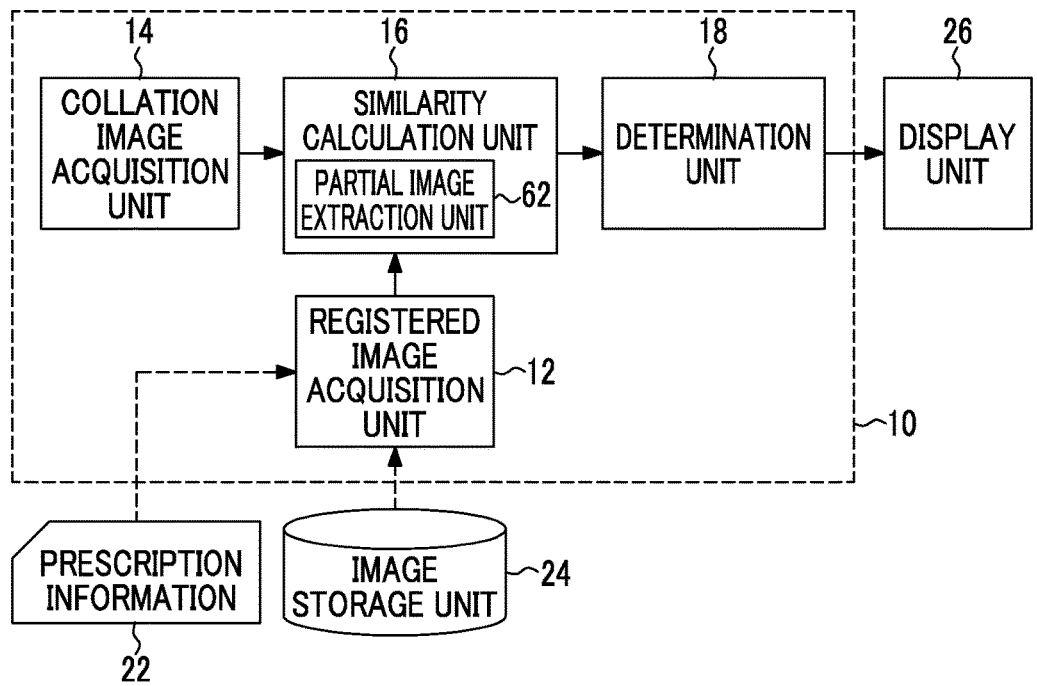

FIG. 14

| No. | NAME OF DRUG SHOWN IN REGISTERED IMAGE | NAME OF DRUG IMAGE FILE | INFORMATION ABOUT IDENTIFICATION INFORMATION (CODE) | | |
|---|---|---|---|---|---|
| | | | PRESENCE OR ABSENCE OF SECANT LINE | INFORMATION ABOUT SIMILAR DRUG | |
| | | | | NAME | POSITION (COORDINATES) WHERE THERE IS DIFFERENCE IN IDENTIFICATION INFORMATION [FEATURE REGION] |
| 1 | ABC | img1.bmp | ABSENCE | DEF | LOWER RIGHT |
| 2 | DEF | img2.bmp | ABSENCE | ABC | LOWER RIGHT |
| 3 | GHI | img3.bmp | PRESENCE | - | - |
| 4 | JKL | img4.bmp | ABSENCE | ABC | LOWER RIGHT |
| | | | | MNO | UPPER LEFT |

FIG. 15A  FIG. 15B  FIG. 15C
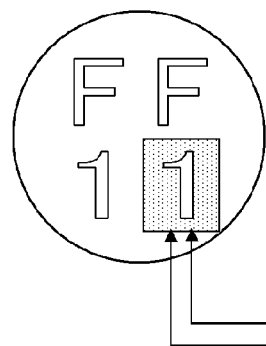
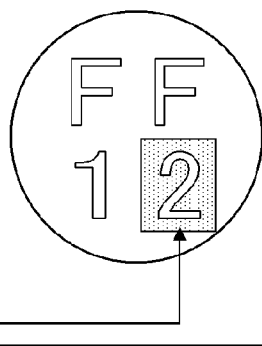
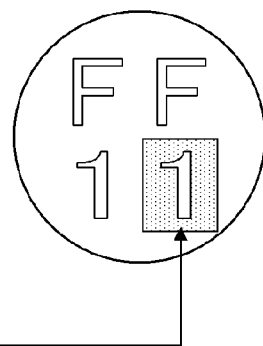
FIG. 16
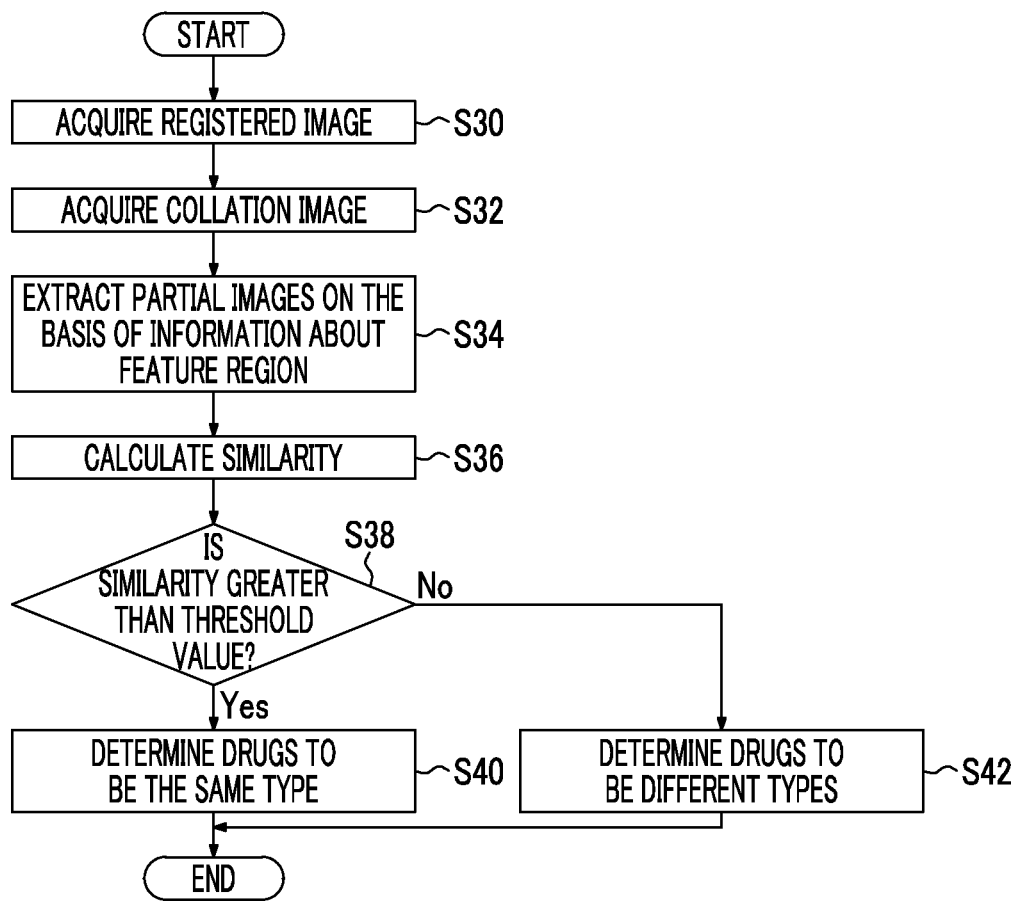

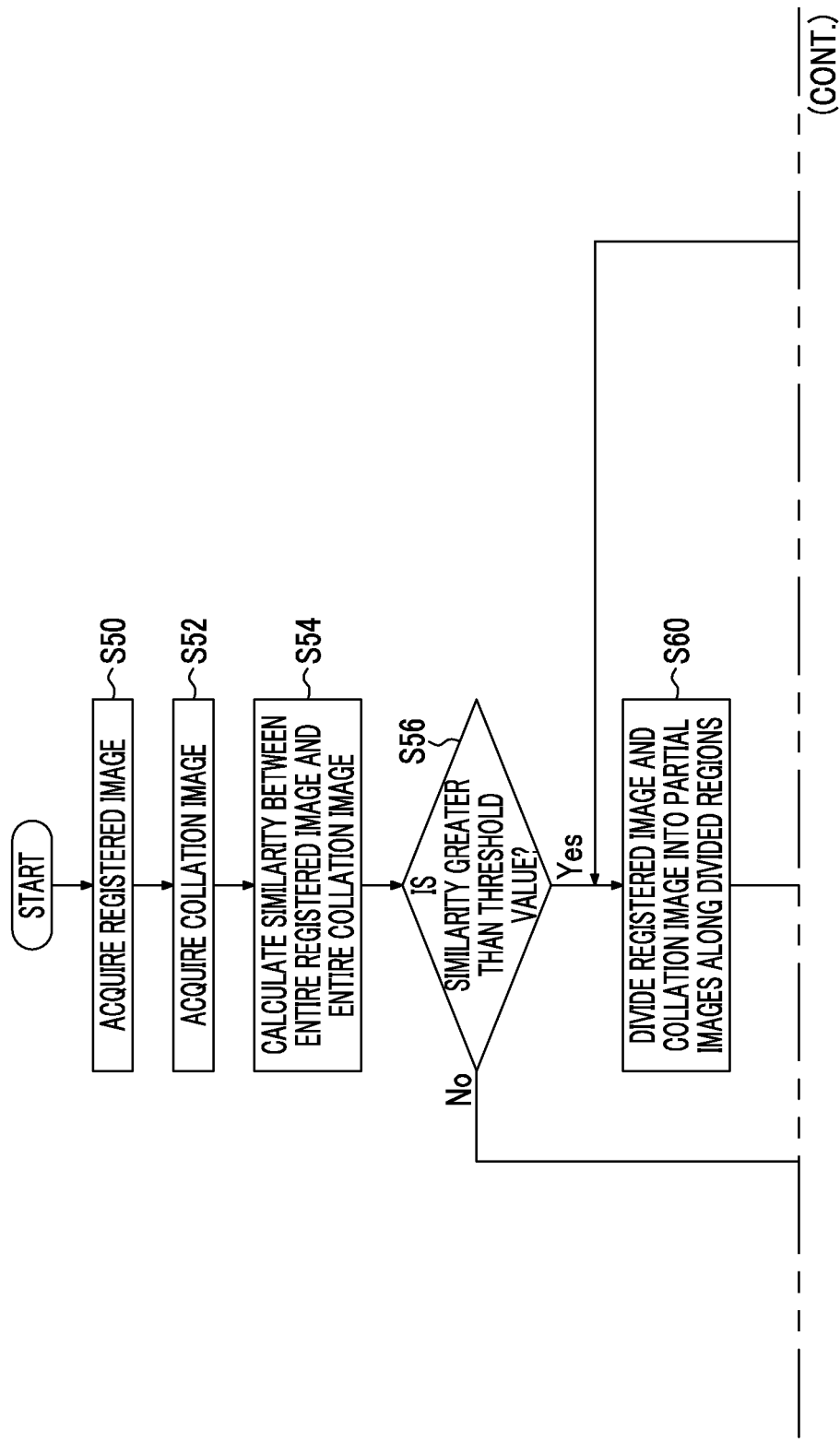

DRUG VERIFICATION DEVICE, DRUG VERIFICATION SYSTEM AND DRUG VERIFICATION METHOD

CROSS-REFERENCE TO RELATED APPLICATIONS

The present application is a Continuation of PCT International Application No. PCT/JP2014/074814 filed on Sep. 19, 2014 claiming priority under 35 U.S.C § 119(a) to Japanese Patent Application No. 2013-199867 filed on Sep. 26, 2013. Each of the above applications is hereby expressly incorporated by reference, in their entirety, into the present application.

BACKGROUND OF THE INVENTION

1. Field of the Invention

The present invention relates to a drug collation device, a drug collation method, and a drug collation system, and more particularly, to a drug collation device, a drug collation method, and a drug collation system which collate drugs using images of the drugs having identification information stamped or printed on the surface thereof.

2. Description of the Related Art

In case in which a pharmacist dispenses and packages drugs according to a prescription in hospitals or drugstores, it is obligatory to check whether the drugs are packaged according to the prescription after packaging. In recent years, various techniques have been considered in order to prevent an artificial checking error in the checking operation or to reduce the burden of the checking operation. For example, a technique has been proposed which captures an image of a drug (tablet), acquires information about the color, size, shape, identification information (identification code) of the drug, collates the acquired information with the information of the drug registered in a server or storage in advance, and specifies the type of the captured drug.

Specifically, JP1993-337168A (JP-H05-337168A) discloses a technique which captures the image of a tablet or a capsule, recognizes the brand of the tablet or the capsule from the captured image, and compares the recognized brand of the tablet or the capsule with the brand of the tablet or the capsule input from an external information processing device or an external terminal.

JP2013-66533A discloses a technique which reads the identification code of a drug in a packet on the basis of images of the drug captured from the upper and lower sides and collates the identification code with the drug dispensed according to a prescription.

JP2013-144101A discloses a technique which matches a master external image with the external shape of a captured drug in a packet to check the image.

JP2010-117331A discloses a technique which matches a cutout image of the captured image of an article to be inspected with a two-dimensional image of a template and then performs stereo matching.

WO2004/112685A discloses a technique which stores an image of a characteristic portion of a drug container and collates the stored image with an acquired image.

SUMMARY OF THE INVENTION

Furthermore, as a representative technical method for collating images, there is a pattern matching method which calculates the similarity between the images using a correlation operation therebetween to collate the images. However, in case in which this method is used with the identification information of drugs, when drugs have similar identification information or there is a secant line in the drugs (tablets), the similarity between images of drugs having different identification information items may be high. As a result, the collation device is likely to output an erroneous determination result.

JP1993-337168A (JP-H05-337168A), JP2013-66533A, JP2013-144101A, JP2010-117331A, and WO2004/112685A do not disclose measures for the problem that, during collation between captured images of drugs, when the drugs have similar identification information or there is a secant line in the drugs, it is difficult to accurately perform the collation.

The invention has been made in view of the above-mentioned problems and an object of the invention is to provide a drug collation device, a drug collation system, and a drug collation method which can accurately collate drugs even in case in which the drugs have similar identification information or there is a secant line in the drugs.

In order to achieve the object, according to an aspect of the invention, there is provided a drug collation device including: a registered image acquisition unit that acquires an image of a drug as a registered image from an image storage unit which stores images of a plurality of types of drug including images of drugs having identification information stamped or printed on the surface thereof, on the basis of prescription information; a collation image acquisition unit that acquires, as a collation image, an image of a drug to be collated with the registered image acquired by the registered image acquisition unit; a similarity calculation unit that calculates similarities between partial images in each corresponding divided region among a plurality of divided regions of the registered image acquired by the registered image acquisition unit and a plurality of divided regions of the collation image acquired by the collation image acquisition unit; and a determination unit that determines whether the drug indicated by the registered image and the drug indicated by the collation image are the same type, on the basis of the lowest similarity among a plurality of similarities which are calculated for each divided region by the similarity calculation unit.

According to this aspect, the similarity between the partial images corresponding to the divided regions is calculated to calculate the similarity between the registered image and the collation image. Therefore, it is possible to accurately collate the drug indicated by the registered image with the drug indicated by the collation image.

Here, the similarity means a value indicating the degree of similarity between images A method for calculating the similarity is not particularly limited and the similarity can be calculated by various methods. For example, it is possible to calculate the similarity using a correlation operation between the images.

Preferably the drug collation device according to the above-mentioned aspect further includes a divided region storage unit that stores information about divided regions predetermined for each registered image or information about divided regions used in all of the registered images. Preferably, the similarity calculation unit specifies the plurality of divided regions on the basis of the information about the divided regions stored in the divided region storage unit.

According to this aspect, the divided regions are specified using the information about predetermined divided regions or the information about the divided regions used in all of the registered images. Therefore, when the divided regions are specified and the partial images are formed, it is possible to reduce the calculation load of image processing.

Preferably, the drug collation device according to the above-mentioned aspect further includes an image processing unit that extracts a region of the identification information stamped or printed on the surface of the drug or a region of a secant line on the surface of the drug from at least one of the registered image and the collation image. Preferably, the similarity calculation unit specifies the plurality of divided regions on the basis of the region of the identification information or the region of the secant line extracted by the image processing unit.

According to this aspect, the divided regions are specified according to the region of the identification information or the region of the secant. Therefore, preferable regions can be set as the divided regions and it is possible to accurately collate the drug indicated by the registered image with the drug indicated by the collation image.

According to another aspect of the invention, there is provided a drug collation device including: a registered image acquisition unit that acquires an image of a drug as a registered image from an image storage unit which stores images of a plurality of types of drugs including an image of a drug having identification information stamped or printed on the surface thereof, on the basis of prescription information; a collation image acquisition unit that acquires, as a collation image, an image of a drug to be collated with the registered image acquired by the registered image acquisition unit; a partial image extraction unit that extracts, as partial images, images in regions corresponding to feature regions, in which there is a difference between the identification information of the drug based on the prescription information and the identification information of a drug that is similar to the drug based on the prescription information, from the registered image acquired by the registered image acquisition unit and the collation image acquired by the collation image acquisition unit; a similarity calculation unit that calculates a similarity between the partial image of the registered image and the partial image of the collation image extracted by the partial image extraction unit; and a determination unit that determines whether the drug indicated by the registered image and the drug indicated by the collation image are the same type, on the basis of the similarity calculated by the similarity calculation unit.

According to this aspect, the similarity between the registered image and the collation image is calculated, using the similarity between the partial images corresponding to the feature regions, and collation is performed using the similarity. Therefore, it is possible to effectively collate the registered image with the collation image.

Here, the feature region means a region which is capable of distinguishing a drug from another type of drug (a region in which there is a difference in identification information) in the identification information of the drug.

Preferably, the partial image extraction unit extracts partial images of the image of the drug that is similar to the drug based on the prescription information. Preferably, the similarity calculation unit calculates the similarity between the partial image of the collation image and the partial image of the image indicating the drug that is similar to the drug based on the prescription information. Preferably, the determination unit determines whether the drug indicated by the collation image and the drug that is similar to the drug based on the prescription information are the same type.

According to this aspect, the collation between the drug shown in the collation image and the drug that is similar to the drug shown in the registered image is performed in addition to the collation between the drug shown in the registered image and the drug shown in the collation image. Therefore, it is possible to effectively perform a collation operation.

Preferably, the drug collation device according to the above-mentioned aspect further includes: a feature region storage unit that stores information about a feature region, which is set in advance for each drug having the identification information stamped or printed on the surface thereof and specifies a region in which there is a difference between the entire image of a drug and the image of another drug similar to the image of the drug, for each drug; and a feature region acquisition unit that acquires the information about the feature region which corresponds to the registered image acquired by the registered image acquisition unit from the feature region storage unit. Preferably, the partial image extraction unit extracts the partial images from the registered image acquired by the registered image acquisition unit and the collation image acquired by the collation image acquisition unit, on the basis of the information about the feature region acquired by the feature region acquisition unit.

According to this aspect, the similarity between the registered image and the collation image is calculated, using the similarity between the partial images corresponding to the feature regions, and collation is performed using the similarity. Therefore, it is possible to effectively collate the registered image with the collation image.

Preferably, in case in which there are a plurality of drugs of which the entire image is similar to the drug indicated by the registered image, the feature region storage unit stores the information about the feature region of each of the plurality of drugs. Preferably, in case in which there are a plurality of drugs which have a similar image to the drug indicated by the registered image acquired by the registered image acquisition unit, the feature region acquisition unit acquires the information about the feature region of each of the plurality of drugs from the feature region storage unit. Preferably, in case in which there are a plurality of drugs which have a similar image to the drug indicated by the registered image acquired by the registered image acquisition unit, the partial image extraction unit extracts corresponding partial images on the basis of the information about the feature region of each of the plurality of drugs acquired by the feature region acquisition unit. Preferably, in case in which there are a plurality of drugs which have a similar image to the drug indicated by the registered image acquired by the registered image acquisition unit, the similarity calculation unit calculates the similarities between the partial images of the registered image and the partial images of the collation image of each of the plurality of drugs extracted by the partial image extraction unit. Preferably, in case in which there are a plurality of drugs which have a similar image to the drug indicated by the registered image acquired by the registered image acquisition unit, the determination unit determines whether the drug indicated by the registered image and the drug indicated by the collation image are the same type, on the basis of the lowest similarity between a plurality of similarities calculated by the similarity calculation unit.

According to this aspect, even in the case of a registered image including a plurality of feature regions, the partial images in each of the plurality of feature regions are extracted and the similarity is calculated using the partial images. Therefore, it is possible to effectively perform collation.

Preferably, the collation image acquisition unit includes a drug image capture unit that captures an image of the drug to be collated to acquire the collation image and an imaging condition setting unit that sets imaging conditions of the drug image capture unit. Preferably, in case in which the determination unit determines that the drug indicated by the registered image and the drug indicated by the collation image are different from each other, the imaging condition setting unit changes the imaging conditions in a range of a plurality of different imaging conditions and the collation image which is captured under the changed imaging conditions is acquired. Preferably, the similarity calculation unit calculates the similarity on the basis of the collation image captured under the changed imaging conditions.

According to this aspect, in case in which the determination unit determines that the drug indicated by the registered image and the drug indicated by the collation image are different from each other, the collation image acquisition unit acquires the collation image captured under the changed imaging conditions and the similarity calculation unit calculates the similarity again. Therefore, it is possible to prevent the determination unit from determining that the drug indicated by the registered image and the drug indicated by the collation image are different from each other even though the drugs are the same.

Preferably, the collation image acquisition unit includes a drug image capture unit that captures an image of the drug to be collated to acquire the collation image and an imaging condition setting unit that sets imaging conditions of the drug image capture unit. Preferably, the imaging condition setting unit sequentially changes the imaging conditions in a range of a plurality of different imaging conditions and the collation images which are captured under each of the changed imaging conditions are acquired. Preferably, the similarity calculation unit calculates the similarities on the basis of the collation images captured under the changed imaging conditions. Preferably, the determination unit selects a representative similarity which is the highest similarity among a plurality of similarities which are calculated under a plurality of imaging conditions in the same divided region and determines whether the drug indicated by the registered image and the drug indicated by the collation image are the same type, on the basis of a final similarity which is the lowest similarity among the representative similarities in each divided region.

According to this aspect, the collation image acquisition unit acquires the collation images captured under a plurality of imaging conditions and the similarity calculation unit calculates a plurality of similarities between the partial images in the same divided region. Therefore, it is possible to prevent the determination unit from determining that the drug indicated by the registered image and the drug indicated by the collation image are different from each other even though the drugs are the same.

Preferably, the collation image acquisition unit includes a drug image capture unit that captures an image of the drug to be collated to acquire the collation image and an imaging condition setting unit that sets imaging conditions of the drug image capture unit. Preferably, the imaging condition setting unit sequentially changes the imaging conditions in a range of a plurality of different imaging conditions and the collation images which are captured under each of the changed imaging conditions are acquired. Preferably, the similarity calculation unit calculates the similarities on the basis of the collation images captured under the changed imaging conditions. Preferably, the determination unit selects a representative similarity which is the highest similarity among a plurality of similarities which are calculated under a plurality of imaging conditions in the feature region and determines whether the drug indicated by the registered image and the drug indicated by the collation image are the same type, on the basis of a final similarity which is the lowest similarity among the representative similarities.

According to this aspect, the collation image acquisition unit acquires the collation images captured under a plurality of imaging conditions and the similarity calculation unit calculates a plurality of similarities between the partial images in the same feature region. Therefore, it is possible to prevent the determination unit from determining that the drug indicated by the registered image and the drug indicated by the collation image are different from each other even though the drugs are the same.

Preferably, the drug collation device according the above-mentioned aspect further includes a preprocessing determination unit that determines whether the registered image acquired by the registered image acquisition unit and the collation image acquired by the collation image acquisition unit are similar to each other as a whole. Preferably, in case in which the preprocessing determination unit determines that the registered image and the collation image are similar to each other, the similarity calculation unit calculates the similarity. Preferably, in case in which the preprocessing determination unit determines that the registered image and the collation image are similar to each other, the determination unit determines whether the drug indicated by the registered image and the drug indicated by the collation image are the same type.

According to this aspect, before the similarity between the partial images is calculated, it is determined whether the registered image and the collation image are similar to each other as a whole. When it is determined that the registered image and the collation image are similar to each other as a whole, the similarity between the partial images of the registered image and the collation image is determined. Therefore, it is possible to improve the efficiency of the collation between the registered image and the collation image. Here, the term "similar to each other as a whole" means that the entire images are similar to each other.

Preferably, the drug collation device according to the above-mentioned aspect further includes a preprocessing determination unit that determines whether the registered image acquired by the registered image acquisition unit and the collation image acquired by the collation image acquisition unit are similar to each other as a whole. Preferably, in case in which the preprocessing determination unit determines that the registered image and the collation image are similar to each other, the partial image extraction unit extracts the image in the feature region as the partial image. Preferably, in case in which the preprocessing determination unit determines that the registered image and the collation image are similar to each other, the similarity calculation unit calculates the similarity. Preferably, in case in which the preprocessing determination unit determines that the registered image and the collation image are similar to each other, the determination unit determines whether the drug indicated by the registered image and the drug indicated by the collation image are the same type.

According to this aspect, before the similarity between the partial images is calculated, it is determined whether the registered image and the collation image are similar to each other as a whole. Therefore, it is possible to improve the efficiency of collation. Here, the term "similar to each other as a whole" means that the entire images are similar to each other.

Preferably, the similarity calculation unit calculates the similarity using a correlation operation between the partial image of the registered image acquired by the registered image acquisition unit and the partial image of the collation image acquired by the collation image acquisition unit.

According to this aspect, the similarity is calculated using the correlation operation. Therefore, it is possible to accurately calculate the similarity.

According still another aspect of the invention, there is provided a drug collation system including: an image storage unit that stores images of a plurality of types of drugs including an image of a drug having identification information stamped or printed on the surface thereof; a registered image acquisition unit that acquires an image of a drug as a registered image from the image storage unit, on the basis of prescription information; a collation image acquisition unit that acquires an image of a drug to be collated as a collation image; a similarity calculation unit that calculates similarities between partial images in corresponding divided regions among a plurality of divided regions of the registered image acquired by the registered image acquisition unit and a plurality of divided regions of the collation image acquired by the collation image acquisition unit; and a determination unit that determines whether the drug indicated by the registered image and the drug indicated by the collation image are the same type, on the basis of the lowest similarity among a plurality of similarities calculated by the similarity calculation unit.

According yet another aspect of the invention, there is provided a drug collation system including: an image storage unit that stores images of a plurality of types of drugs including an image of a drug having identification information stamped or printed on the surface thereof; a registered image acquisition unit that acquires an image of a drug as a registered image from the image storage unit, on the basis of prescription information; a collation image acquisition unit that acquires an image of a drug to be collated as a collation image; a partial image extraction unit that extracts, as partial images, images in regions corresponding to feature regions, in which there is a difference between the identification information of the drug based on the prescription information and the identification information of a drug that is similar to the drug based on the prescription information, from the registered image acquired by the registered image acquisition unit and the collation image acquired by the collation image acquisition unit; a similarity calculation unit that calculates a similarity between the partial image of the registered image and the partial image of the collation image extracted by the partial image extraction unit; and a determination unit that determines whether the drug indicated by the registered image and the drug indicated by the collation image are the same type, on the basis of the similarity calculated by the similarity calculation unit.

According still yet another aspect of the invention, there is provided a drug collation method including: a registered image acquisition step of acquiring an image of a drug as a registered image from an image storage unit which stores images of a plurality of types of drugs including an image of a drug having identification information stamped or printed on the surface thereof, on the basis of prescription information; a collation image acquisition step of acquiring an image of a drug to be collated as a collation image; a similarity calculation step of calculating similarities between partial images in each corresponding divided region among a plurality of divided regions of the registered image acquired in the registered image acquisition step and a plurality of divided regions of the collation image acquired in the collation image acquisition step; and a determination step of determining whether the drug indicated by the registered image and the drug indicated by the collation image are the same type, on the basis of the lowest similarity among a plurality of similarities calculated in the similarity calculation step.

According yet still another aspect of the invention, there is provided a drug collation method including: a registered image acquisition step of acquiring an image of a drug as a registered image from an image storage unit which stores images of a plurality of types of drugs including an image of a drug having identification information stamped or printed on the surface thereof, on the basis of prescription information; a collation image acquisition step of acquiring an image of a drug to be collated as a collation image; a partial image extraction step of extracting, as partial images, images in regions corresponding to feature regions, in which there is a difference between the identification information of the drug based on the prescription information and the identification information of a drug that is similar to the drug based on the prescription information, from the registered image acquired in the registered image acquisition step and the collation image acquired in the collation image acquisition step; a similarity calculation step of calculating a similarity between the partial image of the registered image and the partial image of the collation image extracted in the partial image extraction step; and a determination step of determining whether the drug indicated by the registered image and the drug indicated by the collation image are the same type, on the basis of the similarity calculated in the similarity calculation step.

According to the invention, the collation between drugs is performed on the basis of the similarity between the partial images in the divided regions. Therefore, even in case in which the collation between drugs which have similar identification information or have a secant line on the surface thereof is performed, it is possible to accurately perform the collation. In addition, according to the invention, collation is performed using the similarity between the partial images in the feature regions in which there is a difference between the identification information items of the drugs having similar identification information. Therefore, it is possible to effectively perform the collation.

BRIEF DESCRIPTION OF THE DRAWINGS

FIG. 1 is a functional block diagram illustrating an embodiment of the invention.

FIG. 2 is a diagram illustrating prescription information.

FIG. 6C is a diagram illustrating the division of the registered image and the collation image on the basis of the divided regions.

FIG. 7 is a diagram illustrating the calculation of a similarity.

FIG. 8 is a diagram illustrating a similarity table storing similarities.

FIG. 10 is a diagram illustrating a similarity table storing similarities.

FIG. 11 is a diagram illustrating a similarity table storing similarities.

FIG. 13 is a functional block diagram illustrating another embodiment of the invention.

FIG. 14 is a diagram illustrating information about a feature region.

FIGS. 15A through 15C show a diagram illustrating the calculation of a similarity.

FIG. 16 is a diagram illustrating the flow of an operation according to another embodiment of the invention.

FIGS. 17A and 17B show a diagram illustrating the flow of an operation according to another embodiment of the invention.

DESCRIPTION OF THE PREFERRED EMBODIMENTS

Figure 3:
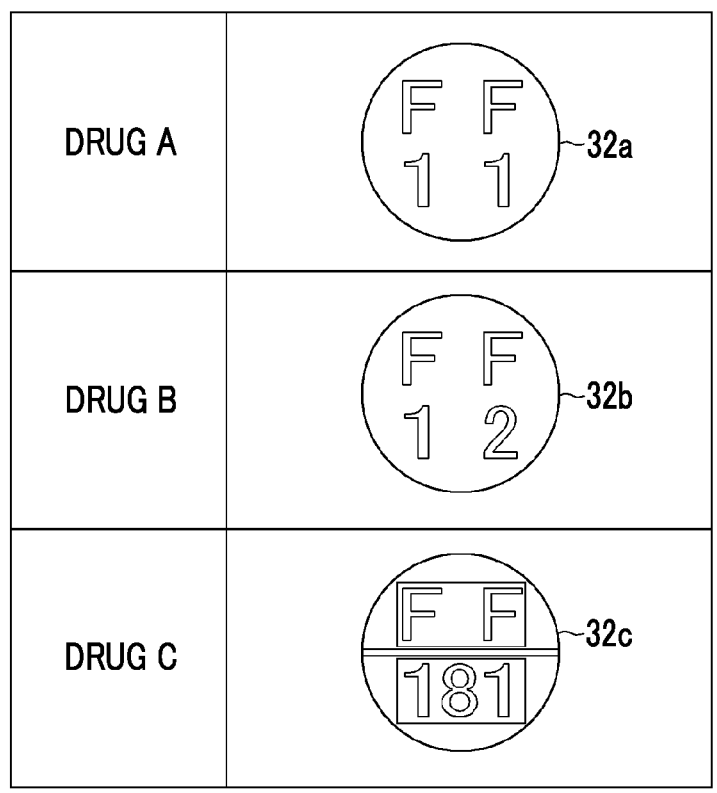
FIG. 3 is a diagram illustrating registered image information.

Hereinafter, embodiments of the invention will be described with reference to the accompanying drawings. For example, a drug collation device 10 which receives prescription information 22 from the outside and is connected to an external image storage unit 24 and a display unit 26 will be described below.

First Embodiment

Hereinafter, a first embodiment of the invention will be described.

FIG. 1 is a functional block diagram illustrating the drug collation device 10. The drug collation device 10 includes a registered image acquisition unit 12, a collation image acquisition unit 14, a similarity calculation unit 16, and a determination unit 18. In addition, the prescription information 22 is input to the registered image acquisition unit 12. The drug collation device 10 is connected to the image storage unit 24 and the display unit 26. In FIG. 1, the functional block is not necessarily separately provided and a plurality of functional blocks may be implemented by hardware and software which are integrally provided.

The registered image acquisition unit 12 acquires the image (hereinafter, referred to as a registered image) of a single type of drug or a plurality of types of drug from the image storage unit 24 which is provided outside the drug collation device 10, on the basis of the prescription information 22. The image storage unit 24 which is provided outside the drug collation device 10 stores the registered images of a plurality of types of drug including the image of a drug having identification information stamped or printed on the surface thereof. A drug database which is generally used in, for example, drugstores or hospitals may be used as the image storage unit 24.

FIG. 2 is a diagram illustrating an example of the prescription information 22. As illustrated in FIG. 2, a prescription 30 is given as an example of the prescription information 22. As illustrated in FIG. 2, the prescription 30 is made such that the patient takes "one tablet of drug A, one tablet of drug B, and one tablet of drug C" after each meal. In addition, information about the drug (in FIG. 2, one tablet of drug A, one tablet of drug B, and one tablet of drug C) to be taken at a time which is written in the prescription 30 is the prescription information 22.

FIG. 3 is a diagram illustrating an example of the registered image which is acquired by the registered image acquisition unit 12 on the basis of the prescription information 22. The registered image acquisition unit 12 acquires a registered image 32a of the drug A, a registered image 32b of the drug B, and a registered image 32c of the drug C from the image storage unit 24 on the basis of the acquired prescription information 22. Then, the registered image acquisition unit 12 transmits the acquired registered images to the similarity calculation unit 16.

The prescription information 22 is input to the registered image acquisition unit 12. However, a method for inputting the prescription information 22 to the registered image acquisition unit 12 is not particularly limited. The prescription information 22 may be transmitted to the registered image acquisition unit 12 wirelessly or through a communication line. In addition, the prescription information 22 may be input to the drug collation device 10 through a user interface (not illustrated) of the drug collation device 10.

How the registered image acquisition unit 12 acquires the registered image from the image storage unit 24 is not particularly limited. For example, the registered image acquisition unit 12 acquires the registered image from the image storage unit 24 through the Internet (including an extranet or an intranet). In addition, in the drug collation device 10 illustrated in FIG. 1, the image storage unit 24 is provided outside the drug collation device 10. However, the image storage unit 24 may be provided in the drug collation device 10.

The collation image acquisition unit 14 (FIG. 1) acquires the image of the drug to be collated as a collation image. The drug to be collated means a packet of drugs which is dispensed on the basis of the prescription information 22 and is taken by the patient. Specifically, the drug to be collated means a packet of drugs which is dispensed by a person or a machine on the basis of the prescription information 22 illustrated in FIG. 2. It is necessary to check whether a packet of drugs which is dispensed as described above is dispensed and packaged on the basis of the prescription information 22. The collation image acquisition unit 14 captures the image of the drug to be collated and acquires the collation image.

Figure 4:
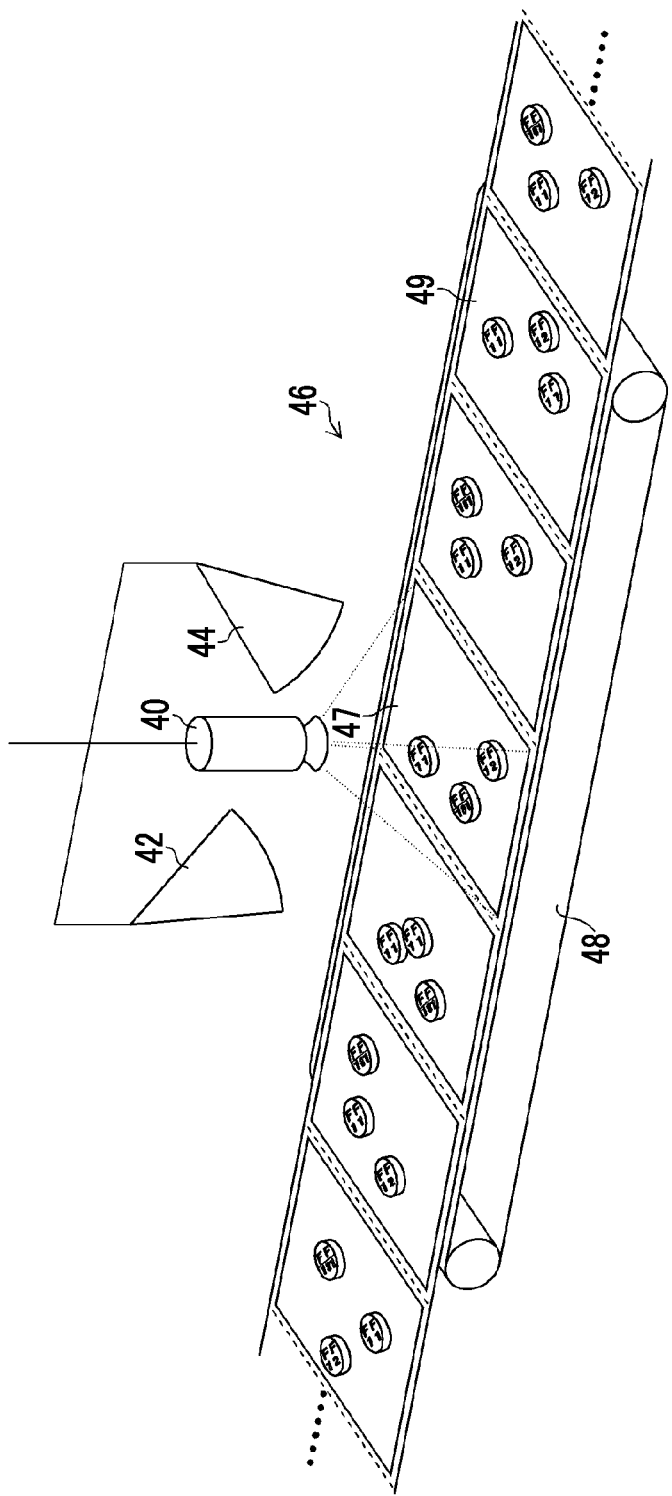
FIG. 4 is a diagram illustrating the acquisition of a collation image.

FIG. 4 is a diagram schematically illustrating an aspect in which the collation image acquisition unit 14 captures the image of the drug to be collated and acquires the collation image. As illustrated in FIG. 4, a camera 40 which is a drug image capture unit captures the images of a series of packets of drugs 46 which are transported by a transport unit 48, using lights 42 and 44. Specifically, the camera 40 captures the collation image of a packet 47 in a series of packets of drugs 46. In addition, each packet in a series of packets of drugs 46 basically includes the drug which is dispensed on the basis of the prescription information 22. However, in some cases, a drug which does not correspond to the prescription information 22 enters a packet for any reason (for example, a packet 49). For convenience of explanation, all of drugs in each packet are illustrated with the top side up. However, in practice, there is a drug which is turned upside down when the collation image is acquired. In this case, for example, a plurality of cameras 40 are provided to capture the image of the drug which is turned upside down.

It is preferable that an imaging condition setting unit (not illustrated) changes the imaging conditions of the drug image capture unit (the camera 40 and the lights 42 and 44) provided in the collation image acquisition unit 14. For example, the imaging condition setting unit can change the setting of the lights 42 and 44 such that light is emitted to the drug at a different angle. In addition, the imaging condition setting unit can adjust the amount of light emitted from the light 42 or the light 44. The imaging condition setting unit can change the setting of the camera 40 to change the imaging conditions. For example, the imaging condition setting unit can adjust, for example, the F number, shutter speed, or International Organization for Standardization (ISO) sensitivity of the camera 40 to change the imaging conditions. In case in which it is difficult to appropriately calculate similarity due to a difference in imaging conditions between the registered image and the collation image, the collation image acquisition unit 14 can change the imaging conditions to acquire the collation image again. In addition, the collation image acquisition unit 14 may acquire a collation image which is acquired by imaging means provided outside the drug collation device 10. That is, the collation image acquisition unit 14 may acquire the collation image captured by an external camera of the drug collation device 10 through, for example, the Internet or a recording medium.

As described above, the registered image acquisition unit 12 acquires the registered image from the image storage unit 24 on the basis of the prescription information 22. In case in which the prescription information 22 illustrated in FIG. 2 is acquired, the registered image acquisition unit 12 acquires the registered images 32a, 32b, and 32c (FIG. 3) corresponding to the drugs A, B, and C from the image storage unit 24.

In case in which a packet of drugs is dispensed according to the prescription information 22, the collation image acquisition unit 14 acquires an image including the drugs A, B, and C. In addition, as preprocessing, the collation image acquisition unit 14 extracts the regions of each drug from the acquired image and acquires the images (in this example, three collation images) of the extracted regions of each drug.

The similarity calculation unit 16 (FIG. 1) calculates the similarity between the registered image acquired by the registered image acquisition unit 12 and the collation image acquired by the collation image acquisition unit 14. In this example, the similarity calculation unit 16 calculates the similarities between the registered images 32a, 32b, and 32c and three collation images Here, the similarity is calculated for a packet of drugs as follows. Three similarities between the registered image 32a and the three collation images are calculated on the basis of the registered image 32a. Similarly, three similarities between the registered image 32b and the three collation images are calculated on the basis of the registered image 32b and three similarities between the registered image 32c and the three collation images are calculated on the basis of the registered image 32c. That is, the similarity calculation unit 16 calculates similarities corresponding to the product of the number of drugs written in the prescription 30 and the number of drugs to be collated (the number of drugs corresponding to one packet to be dispensed).

The similarity calculation unit 16 includes a preprocessing determination unit (not illustrated). In case in which the initial similarity is calculated, the preprocessing determination unit performs the collation between all of the registered images and all of the collation images.

The similarity calculation unit 16 performs, as preprocessing, a process of converting two types of images into grayscale images in order to calculate the similarity between two types of images using normalized cross-correlation. The normalized cross-correlation is not robust with respect to rotation. Therefore, the similarity calculation unit 16 sequentially calculates the similarity using the normalized cross-correlation, while rotating one of the two types of images by a predetermined angle, and sets the highest similarity as the final similarity between all of the images. The preprocessing determination unit calculates the overall similarity between the registered images and the collation images, using the normalized cross-correlation. Then, the preprocessing determination unit determines whether the registered image and the collation image are similar to each other as a whole on the basis of a threshold value. For the value of the similarity, for example, in case in which the maximum value of the similarity is 1, the threshold value can be preferably 0.7, more preferably 0.8, and most preferably 0.9.

In case in which the similarities between all of the registered images and all of the collation images are high (two types of images are similar to each other), the similarity calculation unit 16 divides each of the registered image and the collation image into a plurality of regions and calculates the similarity for each divided region.

Next, the calculation of the similarity for each divided region will be described.

First, a method for dividing each of the registered image and the collation image into a plurality of regions will be described.

Figure 5A:
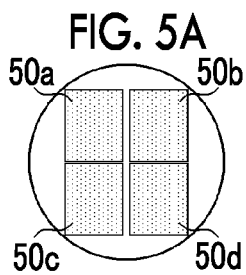
FIG. 5A is a diagram illustrating the division of a registered image and a collation image on the basis of divided regions.
Figure 5B:
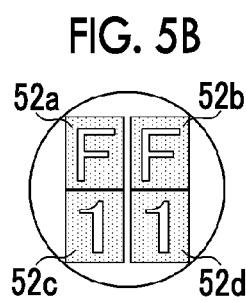
FIG. 5B is a diagram illustrating the division of the registered image and the collation image on the basis of the divided regions.
Figure 5C:
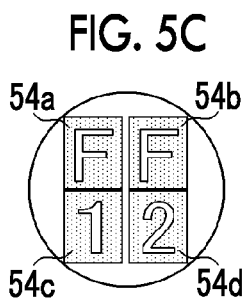
FIG. 5C is a diagram illustrating the division of the registered image and the collation image on the basis of the divided regions.

FIGS. 5A to 5C are diagrams illustrating the division of each of the registered image and the collation image into regions. FIG. 5A illustrates predetermined divided regions. FIG. 5B illustrates the registered image which is divided along the divided regions. FIG. 5C illustrates the collation image which is divided along the divided regions.

As illustrated in FIG. 5A, predetermined divided regions are determined according to the positions at which the identification information of the drug is stamped or printed. That is, the divided regions (50a, 50b, 50c, and 50d) illustrated in FIG. 5A are arranged in two rows and two columns (2×2) according to the identification information which is arranged in two rows and two columns (2×2) on the surface of the drug.

As illustrated in FIG. 5B, the registered image is divided in partial images (52a, 52b, 52c, and 52d) on the basis of the divided regions (50a, 50b, 50c, and 50d). Each of the partial images which are divided on the basis of the divided regions has each identification information item in the registered image.

As illustrated in FIG. 5C, the collation image is divided into partial images (54a, 54b, 54c, and 54d) on the basis of the divided regions (50a, 50b, 50c, and 50d). Each of the partial images which are divided on the basis of the divided regions has each identification information item in the collation image.

Figure 6A:
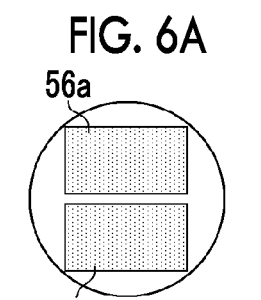
FIG. 6A is a diagram illustrating the division of a registered image and a collation image on the basis of divided regions.
Figure 6B:
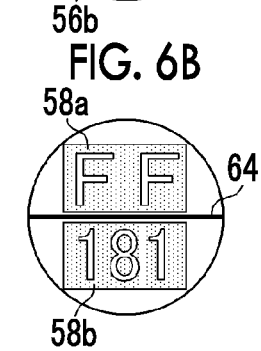
FIG. 6B is a diagram illustrating the division of the registered image and the collation image on the basis of the divided regions.

FIGS. 6A to 6C are diagrams illustrating the division of the registered image and the collation image into regions different from the divided regions illustrated in FIGS. 5A to 5C. FIG. 6A illustrates predetermined divided regions different from those illustrated in FIG. 5A. FIG. 6B illustrates the registered image which is divided on the basis of the divided regions. FIG. 6C illustrates the collation image which is divided on the basis of the divided regions.

The divided regions illustrated in FIG. 6A are determined according to a secant line 64 and the identification information of the drug. That is, the divided regions (56a and 56b) are set so as not to include the secant line 64 of the drug and to include the identification information. As illustrated in FIG. 6B, the registered image is divided into partial images (58a and 58b) on the basis of the divided regions (56a and 56b). Each of the partial images which are divided on the basis of the divided regions has each identification information item and dose not include the secant line.

The similarity calculation unit 16 calculates the similarities between the partial images of the registered image which are divided on the basis of the divided regions and the partial images of the collation image which are divided on the basis of the divided regions. Even in case in which the preprocessing determination unit determines that the entire registered image is similar to the entire collation image, the similarity calculation unit 16 can calculate the similarities between a plurality of divided regions and the determination unit 18 can appropriately perform the collation between the drug indicated by the registered image and the drug indicated by the collation image.

A method for calculating the similarity between two images to be compared is not limited to the method using normalized cross-correlation. Various methods may be considered. For example, the sum of the absolute values of the differences between corresponding pixels of two images may be calculated to calculate the similarity.

As illustrated in FIGS. 5A to 5C and FIGS. 6A to 6C, the divided regions are determined in advance according to the registered image. That is, the registered image (FIG. 5B) of the drug A has the divided regions illustrated in FIG. 5A and the registered image (FIG. 6B) of the drug C has the divided regions illustrated in FIG. 6A. In addition, the divided regions which do not depend on a specific registered image, but are common to all of the registered images may be set.

The similarity calculation unit 16 may include a divided region storage unit (not illustrated) and divide the registered image and the collation image, on the basis of the information of the divided regions predetermined for each registered image or the information of the divided regions used in all of the registered images, which is stored in the divided region storage unit.

The similarity calculation unit 16 may include an image processing unit (not illustrated) and the image processing unit may extract a region of letters which are stamped or printed on the surface of the drug or a region of a secant line on the surface of the drug from at least one of the registered image and the collation image, using binarization or labeling, and may specify the divided regions on the basis of the extraction result. For example, in case in which a registered image in which a secant line is present on the surface of the drug is acquired, the image processing unit extracts the secant line and the similarity calculation unit 16 sets the divided regions such that the secant line is not included in the partial images. In this way, the similarity calculation unit 16 can acquire the partial image corresponding to an identification information region or the partial image which does not include the secant line and thus accurately calculate the similarity.

FIG. 7 is a diagram illustrating the calculation of the similarity between the partial images by the similarity calculation unit 16. The similarity calculation unit 16 calculates the similarity between the partial image 52a of the registered image and the partial image 54a of the collation image, the similarity between the partial image 52b of the registered image and the partial image 54b of the collation image, the similarity between the partial image 52c of the registered image and the partial image 54c of the collation image, and the similarity between the partial image 52d of the registered image and the partial image 54d of the collation image.

The determination unit 18 (FIG. 1) determines whether the drug indicated by the registered image and the drug indicated by the collation image are the same type, on the basis of the lowest similarity among the similarities between a plurality of partial images calculated by the similarity calculation unit 16. That is, the determination unit 18 specifies the lowest similarity among the similarities between the partial images calculated by the similarity calculation unit 16 and uses the lowest similarity as the similarity between the registered image and the image to be collated. Then, the determination unit 18 determines whether the drug indicated by the registered image and the drug indicated by the image to be collated are the same type, on the basis of the similarity. Here, the lowest similarity among the similarities between the partial images corresponding to the divided regions means the final similarity.

FIG. 8 is a diagram illustrating a similarity table in which the similarity calculated by the similarity calculation unit 16 is temporarily stored. The similarities between a plurality of partial images calculated by the similarity calculation unit 16 are temporarily stored in the similarity table provided in the determination unit 18. In addition, the similarity calculation unit 16 may have the similarity table and the determination unit 18 may receive the similarity table from the similarity calculation unit 16.

In the similarity table illustrated in FIG. 8, the similarity between the partial image 52a and the partial image 54a is written in an "upper left" field. Since both the partial image 52a and the partial image 54a indicate a portion (letter), "F", of the identification information, the similarity therebetween is a relatively high value of 0.95. The similarity between the partial image 52b and the partial image 54b is written in an "upper right" field. Since both the partial image 52b and the partial image 54b indicate a portion (letter), "F", of the identification information, the similarity therebetween is a relatively high value of 0.93. The similarity between the partial image 52c and the partial image 54c is written in a "lower left" field. Since both the partial image 52c and the partial image 54c indicate a portion (number), "1", of the identification information, the similarity therebetween is a relatively high value of 0.91. The similarity between the partial image 52d and the partial image 54d is written in a "lower right" field. The partial image 52d indicates a portion (number), "1", of the identification information and the partial image 54d indicates a portion (number), "2", of the identification information. Therefore, the similarity therebetween is a relatively low value of 0.52. The upper left side, the lower left side, the upper right side, and the lower right side indicate an upper left side, a lower left side, an upper right side, and a lower right side in a plan view of FIG. 7, respectively.

The determination unit 18 selects the lowest (minimum) similarity (final similarity) from the similarities between the partial images, with reference to the similarity table. Specifically, in the similarity table illustrated in FIG. 8, the similarity between the partial images (52*a* and 54*a*) on the upper left side is 0.95, the similarity between the partial images (52*b* and 54*b*) on the upper right side is 0.93, the similarity between the partial images (52*c* and 54*c*) on the lower left side is 0.91, and the similarity between the partial images (52*d* and 54*d*) on the lower right side is 0.52. Therefore, the determination unit 18 selects the similarity (0.52) between the partial images (52*d* and 54*d*) on the lower right side as the final similarity.

Then, the determination unit 18 determines whether the drug indicated by the registered image and the drug indicated by the collation image are the same type, on the basis of the final similarity. Specifically, in case in which the final similarity is greater than a threshold value, the determination unit 18 determines that the drug indicated by the registered image and the drug indicated by the collation image are the same type. In case in which the final similarity is equal to or less than the threshold value, the determination unit 18 determines that the drug indicated by the registered image and the drug indicated by the collation image are different types. Here, the threshold value is not particularly limited and various values may be used as the threshold value. For example, in case in which the maximum value of the similarity is 1, the threshold value may be 0.7, preferably 0.8, and more preferably 0.9.

In case in which the final similarity is equal to or less than the threshold value, the determination unit 18 determines that the drug indicated by the registered image and the drug indicated by the collation image are different types. Specifically, in some cases, the determination unit 18 determines the similarity between a registered image illustrated in FIG. 9A and a collation image illustrated in FIG. 9B.

In case in which the final similarity is equal to or less than the threshold value, the imaging conditions of the collation image are not appropriate. In some cases, the identification information of the collation image is not appropriately captured. Specifically, in some cases, the determination unit 18 determines the similarity between the registered image illustrated in FIG. 9A and a collation image illustrated in FIG. 9C. In this case, the drug indicated by the collation image illustrated in FIG. 9C is the same type as the drug indicated by the registered image (FIG. 9A), but the imaging conditions of the collation image are not appropriate. As a result, the identification information of the collation image is not appropriately captured. Therefore, in this case, it is preferable to change the imaging conditions, to acquire a collation image, and to determine similarity. In this case, it is possible to prevent the drug shown in the registered image and the drug shown in the collation image from being determined to be different types due to an unclear collation image, even though the drugs are the same type.

FIG. 10 is a diagram illustrating a similarity table in case in which the drug indicated by the collation image and the drug indicated by the registered image are different types. Specifically, FIG. 10 illustrates the results in case in which the similarity between the registered image illustrated in FIG. 9A and the collation image illustrated in FIG. 9B is calculated by the above-mentioned method. In this case, it is preset to acquire the collation image of which the imaging conditions have been changed three times. Therefore, three similarities are calculated. In the calculation result of the first similarities, the similarity between the partial images on the "lower right" side is 0.52 and is the lowest in the first similarities between the images. In the calculation result of the second similarities, the similarity between the partial images on the "lower right" side is 0.60 and is the lowest in the second similarities between the images. In the calculation result of the third similarities, the similarity between the partial images on the "lower right" side is 0.55 and is the lowest in the third similarities between the images. As such, in case in which the drug indicated by the collation image and the drug indicated by the registered image are different types, even when the similarity is calculated a plurality of times using the collation images which are captured under different imaging conditions, the similarity is maintained at a low value (equal to or less than a threshold value) and the position (in FIG. 10, the "lower right" side) where the similarity is low is the same. The imaging conditions may be changed any number of times. For example, the imaging conditions may be changed three times, five times, or seven times.

As illustrated in FIG. 10, the determination unit 18 selects a representative similarity which is the highest similarity among a plurality of similarities that are calculated under each of a plurality of imaging conditions in the same divided region. Specifically, in the case illustrated in FIG. 10, the maximum value of the similarity on the "upper left" side is 0.95, the maximum value of the similarity on the "upper right" side is 0.93, the maximum value of the similarity on the "lower left" side is 0.94, and the maximum value of the similarity on the "lower right" side is 0.60.

Then, the determination unit 18 determines whether the drug indicated by the registered image and the drug indicated by the collation image are the same type, on the basis of the final similarity which is the lowest similarity among the representative similarities between the partial images corresponding to each divided region. Specifically, in the case illustrated in FIG. 10, since the representative similarity (0.60) on the "lower right" side is the minimum similarity, the final similarity is 0.60.

FIG. 11 is a diagram illustrating a similarity table in case in which the drug indicated by the collation image and the drug indicated by the registered image are the same type. In the similarity table illustrated in FIG. 11, since the imaging conditions of the collation image are not appropriate, the first similarity between the registered image and the collation image is low. In the case illustrated in FIG. 11, the collation image acquisition unit 14 acquires the collation image of which the imaging conditions have been changed a predetermined number of times and the similarity calculation unit 16 calculates the similarity between the partial images in each divided region of each collation image.

Figure 9A:
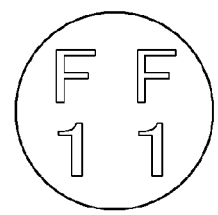
FIG. 9A is a diagram illustrating the registered image
Figure 9B:
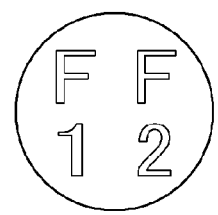
FIG. 9B is a diagram illustrating the collation image.
Figure 9C:
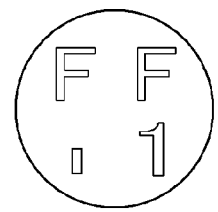
FIG. 9C is a diagram illustrating the collation image.

The similarity table illustrated in FIG. 11 relates to the similarity between the registered image illustrated in FIG. 9A and the collation image illustrated in FIG. 9C. In the registered image illustrated in FIG. 9A, the identification information of the lower left side in a plan view of FIG. 9A is "1". In the collation image illustrated in FIG. 9C, the identification information of the lower left side in a plan view of FIG. 9C is "1". However, since the imaging conditions of the collation image are not appropriate, the identification information "1" is not correctly recognized as illustrated in FIG. 9C. Therefore, the first similarity on the "lower left" side is a low value of 0.55. However, when the collation image acquisition unit 14 acquires the collation image which has been captured while the imaging conditions are changed and the similarity calculation unit 16 calculates the similarity again, the similarity on the "lower left" side is high (the second similarity (0.95) and the third similarity (0.96)).

As illustrated in FIG. 11, the determination unit 18 selects the representative similarity which is the maximum value of the similarity at each position. The maximum value of the similarity on the "upper left" side is 0.94. The maximum value of the similarity on the "upper right" side is 0.95. The maximum value of the similarity on the "lower left" side is 0.96. The maximum value of the similarity on the "lower right" side is 0.94. Then, the determination unit 18 calculates the final similarity which is the lowest similarity among the representative similarities at each position. In the case illustrated in FIG. 11, since the similarities (0.94) on the "upper left" side and the "lower right" side are the minimum similarity, the final similarity is 0.94. Since the final similarity of 0.94 is greater than the threshold value, the determination unit 18 determines that the drug (FIG. 9A) shown in the registered image and the drug (FIG. 9C) shown in the collation image are the same type.

Figure 12:
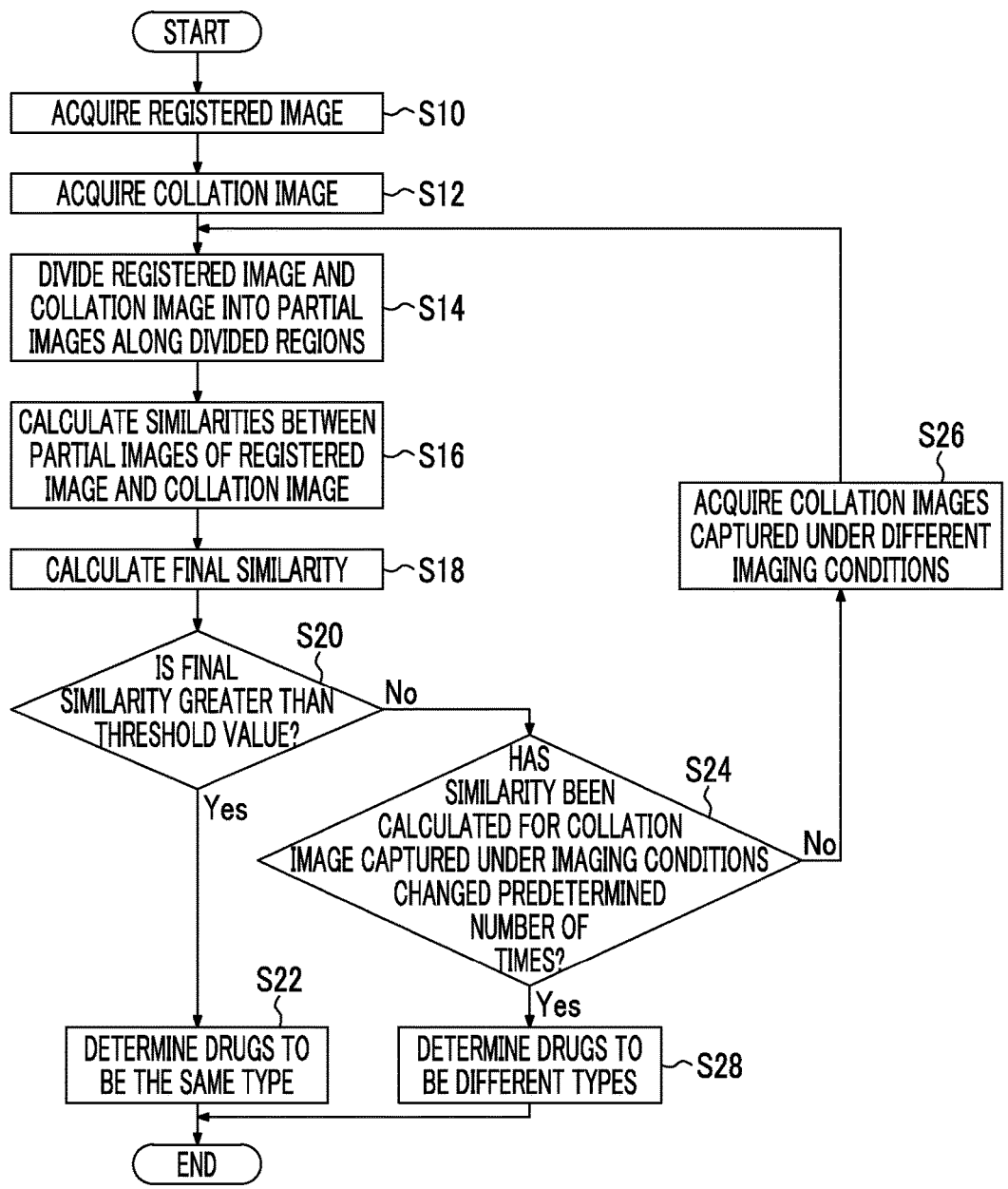
FIG. 12 is a diagram illustrating the flow of an operation according to an embodiment of the invention.

FIG. 12 is a flowchart illustrating the operation of the drug collation device 10. In the operation flowchart illustrated in FIG. 12, the operation flow of the drug collation device 10 in case in which the registered image and the collation image are similar to each other as a whole will be described as a first embodiment.

First, the registered image acquisition unit 12 of the drug collation device 10 acquires the registered image from the external image storage unit 24 on the basis of the prescription information 22 (Step S10). The collation image acquisition unit 14 acquires the collation image (Step S12). Then, the similarity calculation unit 16 divides each of the registered image acquired from the registered image acquisition unit 12 and the collation image acquired from the collation image acquisition unit 14 into partial images on the basis of the divided regions (Step S14). Then, the similarity calculation unit 16 calculates the similarities between the partial images of the registered image and the collation image (Step S16).

Then, the similarity calculation unit 16 calculates the final similarity which is the lowest similarity among the similarities between the partial images of the registered image and the collation image (Step S18). The determination unit 18 determines whether the final similarity is greater than the threshold value (Step S20). In case in which the final similarity is greater than the threshold value (Yes in Step S20), the determination unit 18 determines that the drug shown in the registered image and the drug shown in the collation image are the same type (Step S22).

On the other hand, in case in which the final similarity is equal to or less than the threshold value (No in Step S20), the determination unit 18 determines whether the similarity between the registered image and the collation image, of which the imaging conditions have been changed a predetermined number of times, has been calculated. In case in which the similarity between the registered image and the collation image, of which the imaging conditions have been changed a predetermined number of times, has not been calculated (No in Step S24), the collation image acquisition unit 14 acquires the collation image captured at different imaging conditions (Step S26) and the similarity calculation unit 16 divides each of the registered image and the collation image into partial images again on the basis of the divided regions (Step S14).

On the other hand, in case in which the similarity between the registered image and the collation image, of which the imaging conditions have been changed a predetermined number of times, has been calculated (Yes in Step S24), the determination unit 18 determines that the drug shown in the registered image and the drug shown in the collation image are different from each other (Step S28).

As described above, in the first embodiment, an operation of collating the drug shown in the registered image and the drug shown in the collation image is performed on the basis of the similarities between the partial images which are divided on the basis of the divided regions. Therefore, according to the first embodiment, it is possible to accurately collate the drug shown in the registered image with the drug shown in the collation image.

Second Embodiment

In this embodiment, in case in which the drug shown in the collation image is similar to the drug shown in the registered image, the similarity between the images in feature regions in which there is a difference in identification information between the drugs and it is determined whether the drug shown in the collation image and the drug shown in the registered image are the same type. Therefore, it is possible to reduce the load of similarity calculation in the drug collation device 10. Here, the drug similar to the drug shown in the registered image means a drug which is similar to the drug shown in the registered image. For example, the drug similar to the drug shown in the registered image means a drug that is the same as the drug shown in the registered image in color and shape and is different from the drug shown in the registered image in one or two letters of the identification information (identification code).

In this embodiment, the description of the same structure and operation as those in the first embodiment will not be repeated.

FIG. 13 is a functional block diagram illustrating a drug collation device 10 according to the second embodiment. The drug collation device 10 includes a registered image acquisition unit 12, a collation image acquisition unit 14, a partial image extraction unit 62, a similarity calculation unit 16, and a determination unit 18. The partial image extraction unit 62 is provided in the similarity calculation unit 16. In FIG. 13, the functional block is not necessarily separately provided and a plurality of functional blocks may be implemented by hardware and software which are integrally provided.

The partial image extraction unit 62 extracts partial images from each of the image to be collated and the registered image. Specifically, the partial image extraction unit 62 extracts, as the partial image, images in regions corresponding to the feature regions in which there is a difference between the identification information of the drug based on the prescription information 22 and another drug that is similar to the drug based on the prescription information 22. Here, the feature region means a region including the identification information in which there is a difference between the identification information items of drugs. In other words, the feature region means a partial region in which there is a difference between the identification information items of the drug to be collated and a drug similar to the drug to be collated.

The partial image extraction unit 62 may acquire information about the feature region using various methods. For example, in case in which the registered image acquisition unit 12 acquires the registered image from the image storage unit 24 on the basis of the prescription information 22, the registered image acquisition unit 12 may acquire the information about the feature region from the image storage unit 24, in addition to the registered image, and the partial image extraction unit 62 may acquire the information about the feature region from the registered image acquisition unit 12.

The drug collation device 10 may include a feature region storage unit (not illustrated) that stores the information about the feature region and a feature region acquisition unit (not illustrated) which acquires the information about the feature region from the feature region storage unit. The feature region storage unit stores the information about the feature region for specifying a region, in which there is a difference between the entire image of a drug and the image of another drug similar to the image of the drug, for each drug. The feature region acquisition unit acquires the information about the feature region which corresponds to the registered image acquired by the registered image acquisition unit 12 from the feature region storage unit.

FIG. 14 is a diagram illustrating the data structure of the information about the feature region which is stored in the feature region storage unit. The information about the feature region illustrated in FIG. 14 includes the name of the drug shown in the registered image, the name of a registered image file, and information about identification information. In the case of a drug "ABC" shown in the registered image, the name of a drug image file is "img1.bmp". The drug "ABC" does not have a secant line on the surface thereof and is similar to a drug "DEF". In addition, coordinate information (position) indicating a region in which there is a difference between the identification information (identification code) of the drug "ABC" and the identification information (identification code) of the "DEF" is coordinate information indicating the "lower right" side. In the relationship between the drug "ABC" and the drug "DEF", the feature region is a "lower right" region.

In the case of the drug "DEF" shown in the registered image, the name of a drug image file is "img2.bmp". The drug "DEF" does not have a secant line on the surface thereof and is similar to the drug "ABC". The feature region in which there is a difference between the identification information (identification code) of the drug "ABC" and the identification information (identification code) of the "DEF" is a "lower right" region.

In the case of a drug "GHI" shown in the registered image, the name of a drug image file is "img3.bmp". In addition, the drug "GHI" has a secant line on the surface thereof.

In the case of a drug "JKL" shown in the registered image, the name of a drug image file is "img4.bmp". The drug "JKL" does not have a secant line on the surface thereof and is similar to the drug "ABC" and a drug "MNO". In the relationship between the drug "JKL" and the drug "ABC", the "lower right" region is the feature region. In the relationship between the drug "JKL" and the drug "MNO", the "upper left" region is the feature region. As such, in case in which there are a plurality of drugs, which are similar to the drug shown in the registered image, in all of the images, it is preferable that the information about the feature region of each of the plurality of drugs different from the drug shown in the registered image is stored.

FIGS. 15A through 15C show a diagram illustrating the calculation of the similarity between the partial images, which are extracted by the partial image extraction unit 62, by the similarity calculation unit 16. FIG. 15A illustrates a collation image, FIG. 15B illustrates a registered image, and FIG. 15C illustrates a drug image similar to the registered image. The similarity calculation unit 16 calculates the similarity between the partial images extracted by the partial image extraction unit 62. That is, in the relationship between the drug "ABC" and the drug "DEF", the lower right region is the feature region on the basis of the information about the feature region illustrated in FIG. 14. Therefore, the similarity calculation unit 16 calculates the similarity between the partial image related to the lower right region (collation image) of FIG. 15A and the partial image related to the lower right region (registered image) of FIG. 15B. Then, the determination unit 18 determines whether the drug indicated by the collation image and the drug indicated by the registered image are the same type on the basis of the similarity. The upper left side, the lower left side, the upper right side, and the lower right side indicate an upper left side, a lower left side, an upper right side, and a lower right side in a plan view of FIGS. 15A through 15C, respectively.

As another aspect, the similarity between partial images in a feature region related to the collation image (FIG. 15A) and the registered image (FIG. 15B) and the similarity between partial images in a feature region related to the drug image (FIG. 15C) similar to the collation image (FIG. 15A) and the registered image may be calculated and the determination unit 18 may perform the determination for the collation image on the basis of the similarities. That is, the similarity between the partial images in the feature region of each of the collation image (FIG. 15A), the registered image (FIG. 15B), and the drug image (FIG. 15C) similar to the collation image (FIG. 15A) and the registered image and the drug shown in the collation image may be determined to be the same type as the drug shown in the image with higher similarity (the registered image or the drug image similar to the registered image). In this case, it is possible to perform the collation between the drug shown in the collation image and the drug similar to the drug shown in the registered image as well as the collation between the drug shown in the collation image and the drug shown in the registered image. Therefore, it is possible to effectively perform collation.

FIG. 16 is a flowchart illustrating the operation of the drug collation device 10 according to the second embodiment. In the operation flowchart illustrated in FIG. 16, the operation flow of the drug collation device 10 in case in which the registered image and the collation image are similar to each other as a whole will be described as the second embodiment.

First, the registered image acquisition unit 12 acquires the registered image (Step S30) and the collation image acquisition unit 14 acquires the collation image (Step S32). Then, the partial image extraction unit 62 extracts the partial images in the feature regions of the registered image and the collation image (Step S34). Then, the partial image extraction unit 62 calculates the similarity between the extracted partial images (Step S36).

Then, the determination unit 18 determines whether the similarity calculated by the similarity calculation unit 16 is greater than a threshold value (Step S38). In case in which the similarity is greater than the threshold value (Yes in Step S38), the determination unit 18 determines that the drugs shown in the collation image and the registered image are the same type (Step S40). In case in which the similarity is equal to or less than the threshold value (No in Step S38), the determination unit 18 determines that the drugs shown in the collation image and the registered image are different types (Step S42).

In case in which the similarity is less than the threshold value (No in Step S38), the similarity may be calculated on the basis of the collation image obtained by capturing the image of the drug to be collated while changing the imaging conditions (see Steps S24 and S26 in FIG. 12).

As described above, in the second embodiment, the partial images corresponding to the feature region are extracted and the collation between the drug shown in the registered image and the drug shown in the collation image is performed on the basis of the similarity between the partial images. Therefore, according to the second embodiment, it is possible to effectively collate the registered image with the collation image.

Third Embodiment

In this embodiment, before the collation described in the first embodiment or the second embodiment is performed, the similarity between the entire collation image and the entire registered image is determined. In case in which the similarity is greater than a threshold value, the collation described in the first embodiment or the second embodiment is performed. Therefore, the determination of the similarity between the partial images is not performed for the registered image and the collation image which are distinctly different from each other. As a result, it is possible to effectively perform collation.

Figure 17B:
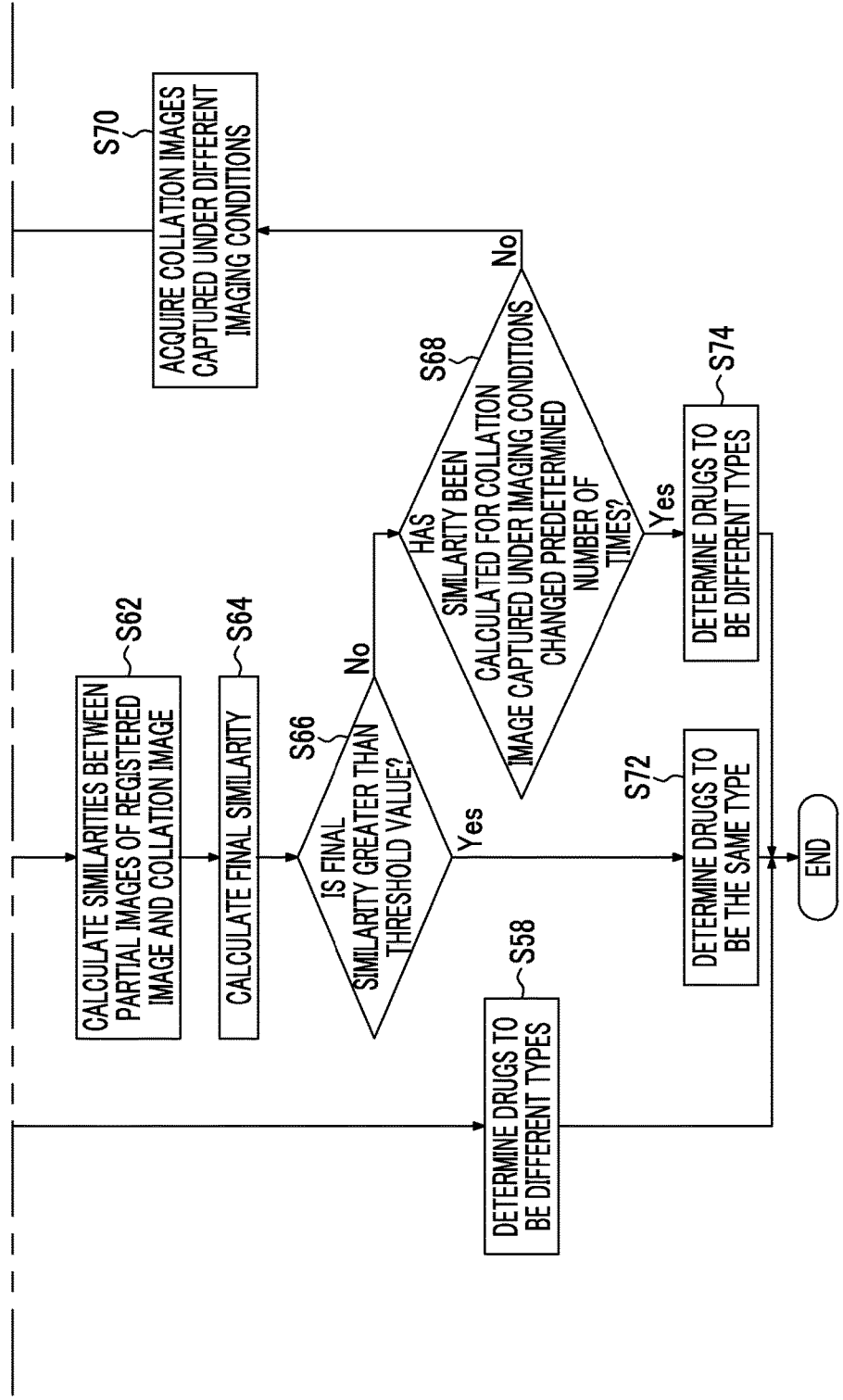

FIGS. 17A and 17B show an operation flowchart illustrating the process described in the first embodiment in case in which a preprocessing determination unit determines that a registered image and a collation image are similar to each other as a whole.

First, the registered image acquisition unit 12 acquires the registered image (Step S50) and the collation image acquisition unit 14 acquires the collation image (Step S52). Then, the preprocessing determination unit performs preprocessing, such as the detection of a drug region or grayscaling, for the registered image and the collation image such that similarity is calculated. Then, the preprocessing determination unit calculates the similarity between the entire registered image and the entire collation image (Step S54). At that time, the similarity is calculated while one of the registered image and the collation image is being rotated by a predetermined angle and the highest similarity value is used as the similarity. In addition, when the similarity is calculated in the subsequent process, it is not necessary to rotate the image by a predetermined angle again since the direction of the images has been set in Step S54. Then, the preprocessing determination unit determines whether the similarity is greater than a threshold value (Step S56).

In case in which the similarity is equal to or less than the threshold value (No in Step S56), the preprocessing determination unit determines that the drugs indicated by the registered image and the collation image are different from each other (Step S58). On the other hand, in case in which the similarity is greater than the threshold value (Yes in Step S56), the process described in the first embodiment is performed (see FIG. 12).

Specifically, the similarity calculation unit 16 forms partial images (Step S60). The similarity calculation unit 16 calculates the similarity between the partial images (Step S62). Then, the similarity calculation unit 16 calculates the final similarity (Step S64). The determination unit 18 determines whether the final similarity is greater than the threshold value (Step S66). In case in which the determination unit 18 determines that the final similarity is greater than the threshold value (Yes in Step S66), the determination unit 18 determines that the drugs indicated by the collation image and the registered image are the same type (Step S72). On the other hand, in case in which the determination unit 18 final similarity is equal to or less than the threshold value (No in Step S66), the determination unit 18 determines whether the similarity between the registered image and the collation image, of which the imaging conditions have been changed a predetermined number of times, has been calculated (Step S68). In case in which the determination unit 18 determines that the similarity between the registered image and the collation image, of which the imaging conditions have been changed a predetermined number of times, has not been calculated (No in Step S68), the collation image acquisition unit 14 acquires a collation image captured at different imaging conditions (Step S70). On the other hand, in case in which the determination unit 18 determines that the similarity between the registered image and the collation image, of which the imaging conditions have been changed a predetermined number of times, has been calculated (Yes in Step S68), the determination unit 18 determines that the drugs shown in the registered image and the collation image are different types (Step S74).

Figure 18:
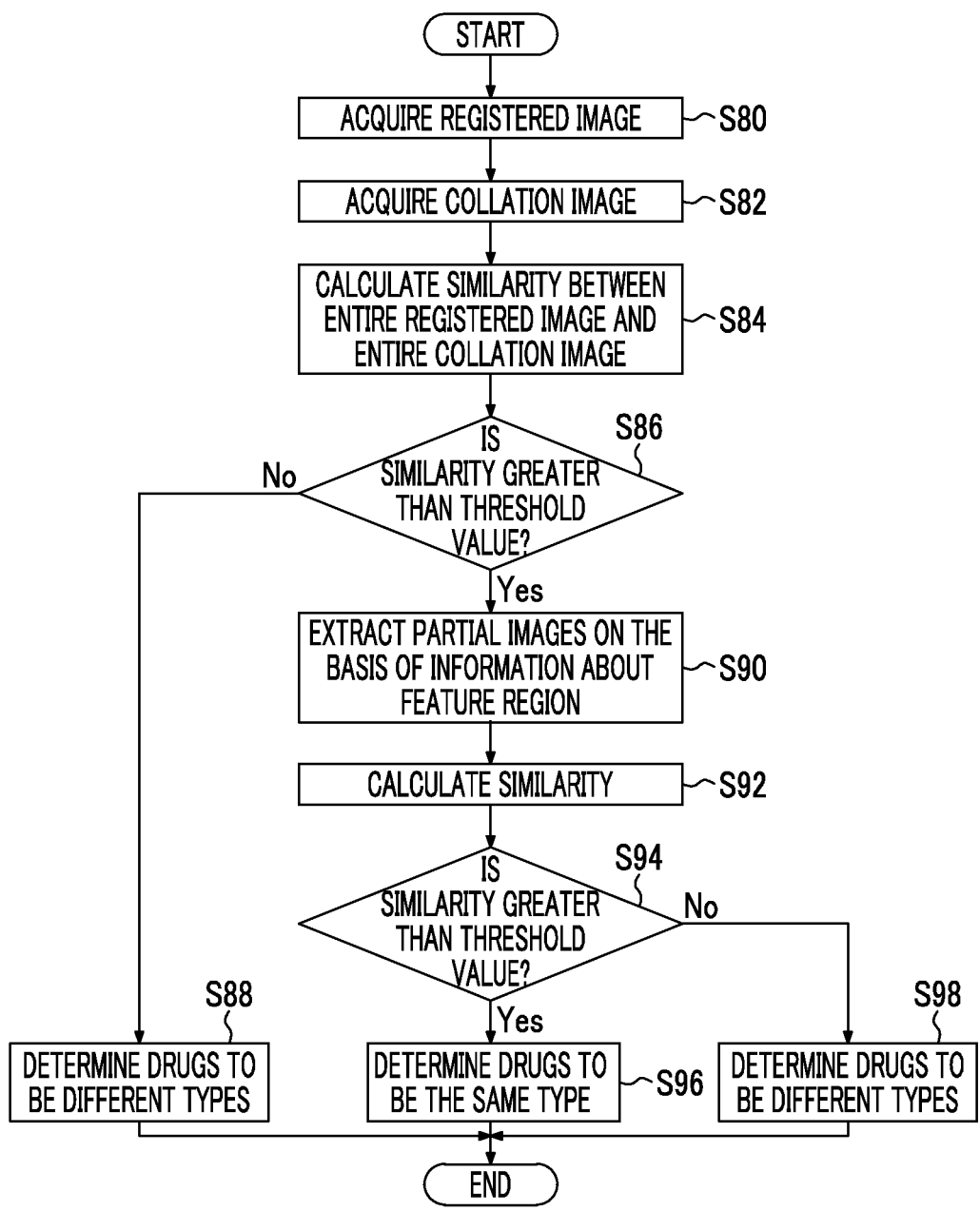
FIG. 18 is a diagram illustrating the flow of an operation according to another embodiment of the invention.

FIG. 18 is an operation flowchart illustrating the process described in the second embodiment in case in which the preprocessing determination unit determines that the registered image and the collation image are similar to each other as a whole.

First, the registered image acquisition unit 12 acquires the registered image (Step S80) and the collation image acquisition unit 14 acquires the collation image (Step S82). Then, the preprocessing determination unit performs preprocessing, such as the detection of a drug region or grayscaling, for the registered image and the collation image such that similarity is calculated. Then, the preprocessing determination unit calculates the similarity between the entire registered image and the entire collation image (Step S84). At that time, the similarity is calculated while one of the registered image and the collation image is being rotated by a predetermined angle and the highest similarity value is used as the similarity. In addition, when the similarity is calculated in the subsequent process, it is not necessary to rotate the image by a predetermined angle again since the direction of the images has been set in Step S84. Then, the preprocessing determination unit determines whether the similarity is greater than the threshold value (Step S86).

In case in which the preprocessing determination unit determines that the similarity is equal to or less than the threshold value (No in Step S86), the preprocessing determination unit determines that the drugs indicated by the registered image and the collation image are different from each other (Step S88). On the other hand, in case in which the preprocessing determination unit determines that the similarity is greater than the threshold value (Yes in Step S86), the process described in the second embodiment is performed (see FIG. 16).

Specifically, the partial image extraction unit 62 extracts the partial images (Step S90). Then, the similarity calculation unit 16 calculates the similarity between the partial images (Step S92). Then, the determination unit 18 determines whether the similarity is greater than the threshold value (Step S94). In case in which the determination unit 18 determines that the similarity is greater than the threshold value (Yes in Step S94), the determination unit 18 determines that the drug shown in the registered image and the drug shown in the collation image are the same (Step S96). In case in which the determination unit 18 determines that the similarity is equal to or less than the threshold value (No in Step S94), the determination unit 18 determines that the drug shown in the registered image and the drug shown in the collation image are different from each other (Step S98).

Other Embodiments

The drug collation device 10 has been mainly described above. However, the invention is not limited thereto. For example, the invention may include embodiments of, for example, a drug collation method and a drug collation system for implementing the invention.

The invention is not limited to the above-described embodiments and various modifications and changes of the invention can be made without departing from the scope and spirit of the invention.

EXPLANATION OF REFERENCES

10: drug collation device
12: registered image acquisition unit
14: collation image acquisition unit
16: similarity calculation unit
18: determination unit
22: prescription information
24: image storage unit
26: display unit
30: prescription
32a: registered image
32b: registered image
40: camera
42: light
44: light
62: partial image extraction unit

What is claimed is:

1. A drug collation device comprising at least one processor having:
   a registered image acquisition process unit that acquires an image of a drug as a registered image from an image storage unit which stores images of a plurality of types of drugs including an image of a drug having identification information stamped or printed on the surface thereof, on the basis of prescription information;
   a collation image acquisition process unit that acquires, as a collation image, an image of a drug to be collated with the registered image acquired by the registered image acquisition process unit;
   a similarity calculation process unit that calculates similarities between partial images in each corresponding divided region among a plurality of divided regions of the registered image acquired by the registered image acquisition process unit and a plurality of divided regions of the collation image acquired by the collation image acquisition process unit; and
   a determination process unit that determines whether the drug indicated by the registered image and the drug indicated by the collation image are the same type, on the basis of the lowest similarity among a plurality of similarities which are calculated for each of the plurality of divided region by the similarity calculation process unit, and
   wherein the similarity calculation unit calculates the similarity using a correlation operation between the partial image of the registered image acquired by the registered image acquisition unit and the partial image of the collation image acquired by the collation image acquisition unit, and wherein the determination process unit uses the lowest similarity value as a basis of comparison with a threshold value.

2. The drug collation device according to claim 1, further comprising:
   a divided region storage unit that stores information about divided regions predetermined for each registered image or information about divided regions used in all of the registered images,
   wherein the similarity calculation unit specifies the plurality of divided regions on the basis of the information about the divided regions stored in the divided region storage unit.

3. The drug collation device according to claim 1, further comprising:
   an image processing unit that extracts a region of the identification information stamped or printed on the surface of the drug or a region of a secant line on the surface of the drug from at least one of the registered image and the collation image,
   wherein the similarity calculation unit specifies the plurality of divided regions on the basis of the region of the identification information or the region of the secant line extracted by the image processing unit.

4. The drug collation device according to claim 1,
   wherein the collation image acquisition unit includes a drug image capture unit that captures an image of the drug to be collated to acquire the collation image and an imaging condition setting unit that sets imaging conditions of the drug image capture unit,
   in case in which the determination unit determines that the drug indicated by the registered image and the drug indicated by the collation image are different from each other, the imaging condition setting unit changes the imaging conditions in a range of a plurality of different imaging conditions and the collation image which is captured under the changed imaging conditions is acquired, and
   the similarity calculation unit calculates the similarity on the basis of the collation image captured under the changed imaging conditions.

5. The drug collation device according to claim 1,
   wherein the collation image acquisition unit includes a drug image capture unit that captures an image of the drug to be collated to acquire the collation image and an imaging condition setting unit that sets imaging conditions of the drug image capture unit,
   the imaging condition setting unit sequentially changes the imaging conditions in a range of a plurality of different imaging conditions and the collation images which are captured under each of the changed imaging conditions are acquired,
   the similarity calculation unit calculates the similarities on the basis of the collation images captured under the changed imaging conditions, and
   the determination unit selects a representative similarity which is the highest similarity among a plurality of similarities which are calculated under a plurality of imaging conditions in the same divided region and determines whether the drug indicated by the registered image and the drug indicated by the collation image are the same type, on the basis of a final similarity which is the lowest similarity among the representative similarities in each divided region.

6. The drug collation device according to claim 1, further comprising:
   a preprocessing determination unit that determines whether the registered image acquired by the registered image acquisition unit and the collation image acquired by the collation image acquisition unit are similar to each other as a whole,
   wherein, in case in which the preprocessing determination unit determines that the registered image and the collation image are similar to each other, the similarity calculation unit calculates the similarity, and in case in which the preprocessing determination unit determines that the registered image and the collation image are similar to each other, the determination unit determines whether the drug indicated by the registered image and the drug indicated by the collation image are the same type.

7. A drug collation device according to claim 1, wherein the at least one processor further includes:
a partial image extraction process unit that extracts, as partial images, images in regions corresponding to feature regions, in which there is a difference between the identification information of the drug based on the prescription information and the identification information of a drug that is similar to the drug based on the prescription information, from the registered image acquired by the registered image acquisition process unit and the collation image acquired by the collation image acquisition process unit;
wherein the similarity calculation process unit further calculates a similarity between the partial image of the registered image and the partial image of the collation image extracted by the partial image extraction process unit; and
the determination process unit that determines whether the drug indicated by the registered image and the drug indicated by the collation image are the same type, on the basis of the similarity calculated by the similarity calculation process unit.

8. The drug collation device according to claim 7, wherein the partial image extraction unit extracts partial images of the image of the drug that is similar to the drug based on the prescription information,
the similarity calculation unit calculates the similarity between the partial image of the collation image and the partial image of the image indicating the drug that is similar to the drug based on the prescription information, and
the determination unit determines whether the drug indicated by the collation image and the drug that is similar to the drug based on the prescription information are the same type.

9. The drug collation device according to claim 7, further comprising:
a feature region storage unit that stores information about a feature region, which is set in advance to each drug having the identification information stamped or printed on the surface thereof and specifies a region in which there is a difference between the entire image of a drug and the image of another drug similar to the image of the drug, for each drug; and
a feature region acquisition unit that acquires the information about the feature region which corresponds to the registered image acquired by the registered image acquisition unit from the feature region storage unit,
wherein the partial image extraction unit extracts the partial images from the registered image acquired by the registered image acquisition unit and the collation image acquired by the collation image acquisition unit, on the basis of the information about the feature region acquired by the feature region acquisition unit.

10. The drug collation device according to claim 9, wherein, in case in which there are a plurality of drugs of which the entire image is similar to the drug indicated by the registered image, the feature region storage unit stores the information about the feature region of each of the plurality of drugs,
in case in which there are a plurality of drugs which have a similar image to the drug indicated by the registered image acquired by the registered image acquisition unit, the feature region acquisition unit acquires the information about the feature region of each of the plurality of drugs from the feature region storage unit,
in case in which there are a plurality of drugs which have a similar image to the drug indicated by the registered image acquired by the registered image acquisition unit, the partial image extraction unit extracts corresponding partial images on the basis of the information about the feature region of each of the plurality of drugs acquired by the feature region acquisition unit,
in case in which there are a plurality of drugs which have a similar image to the drug indicated by the registered image acquired by the registered image acquisition unit, the similarity calculation unit calculates the similarities between the partial images of the registered image and the partial images of the collation image of each of the plurality of drugs extracted by the partial image extraction unit, and
in case in which there are a plurality of drugs which have a similar image to the drug indicated by the registered image acquired by the registered image acquisition unit, the determination unit determines whether the drug indicated by the registered image and the drug indicated by the collation image are the same type, on the basis of the lowest similarity between a plurality of similarities calculated by the similarity calculation unit.

11. The drug collation device according to claim 7, wherein the collation image acquisition unit includes a drug image capture unit that captures an image of the drug to be collated to acquire the collation image and an imaging condition setting unit that sets imaging conditions of the drug image capture unit,
in case in which the determination unit determines that the drug indicated by the registered image and the drug indicated by the collation image are different from each other, the imaging condition setting unit changes the imaging conditions in a range of a plurality of different imaging conditions and the collation image which is captured under the changed imaging conditions is acquired, and
the similarity calculation unit calculates the similarity on the basis of the collation image captured under the changed imaging conditions.

12. The drug collation device according to claim 7, wherein the collation image acquisition unit includes a drug image capture unit that captures an image of the drug to be collated to acquire the collation image and an imaging condition setting unit that sets imaging conditions of the drug image capture unit,
the imaging condition setting unit sequentially changes the imaging conditions in a range of a plurality of different imaging conditions and the collation images which are captured under each of the changed imaging conditions are acquired,
the similarity calculation unit calculates the similarities on the basis of the collation images captured under the changed imaging conditions, and
the determination unit selects a representative similarity which is the highest similarity among a plurality of similarities which are calculated under a plurality of imaging conditions in the feature region and determines whether the drug indicated by the registered image and the drug indicated by the collation image are the same type, on the basis of a final similarity which is the lowest similarity among the representative similarities.

13. The drug collation device according to claim 7, further comprising:
a preprocessing determination unit that determines whether the registered image acquired by the registered image acquisition unit and the collation image acquired by the collation image acquisition unit are similar to each other as a whole,
wherein, in case in which the preprocessing determination unit determines that the registered image and the collation image are similar to each other, the partial image extraction unit extracts the image in the feature region as the partial image,
in case in which the preprocessing determination unit determines that the registered image and the collation image are similar to each other, the similarity calculation unit calculates the similarity, and
in case in which the preprocessing determination unit determines that the registered image and the collation image are similar to each other, the determination unit determines whether the drug indicated by the registered image and the drug indicated by the collation image are the same type.

14. The drug collation device according to claim 7, wherein the similarity calculation unit calculates the similarity using a correlation operation between the partial image of the registered image acquired by the registered image acquisition unit and the partial image of the collation image acquired by the collation image acquisition unit.

15. A drug collation system comprising:
an image storage unit that stores images of a plurality of types of drugs including an image of a drug having identification information stamped or printed on the surface thereof; and
at least one processor having;
a registered image acquisition process unit that acquires an image of a drug as a registered image from the image storage unit, on the basis of prescription information;
a collation image acquisition process unit that acquires an image of a drug to be collated as a collation image;
a similarity calculation process unit that calculates similarities between partial images in corresponding divided regions among a plurality of divided regions of the registered image acquired by the registered image acquisition process unit and a plurality of divided regions of the collation image acquired by the collation image acquisition process unit; and
a determination process unit that determines whether the drug indicated by the registered image and the drug indicated by the collation image are the same type, on the basis of the lowest similarity among a plurality of similarities calculated by the similarity calculation process unit, and
wherein the similarity calculation unit calculates the similarity using a correlation operation between the partial image of the registered image acquired by the registered image acquisition unit and the partial image of the collation image acquired by the collation image acquisition unit, and wherein the determination process unit uses the lowest similarity value as a basis of comparison with a threshold value.

16. A drug collation system according to claim 15, wherein the at least one processor further comprises:
a partial image extraction process unit that extracts, as partial images, images in regions corresponding to feature regions, in which there is a difference between the identification information of the drug based on the prescription information and the identification information of a drug that is similar to the drug based on the prescription information, from the registered image acquired by the registered image acquisition process unit and the collation image acquired by the collation image acquisition process unit; and
the similarity calculation process unit that further calculates a similarity between the partial image of the registered image and the partial image of the collation image extracted by the partial image extraction process unit; and
the determination process unit that determines whether the drug indicated by the registered image and the drug indicated by the collation image are the same type, on the basis of the similarity calculated by the similarity calculation process unit.

17. A drug collation method executed by at least one processor comprising:
a registered image acquisition step of acquiring an image of a drug as a registered image from an image storage unit which stores images of a plurality of types of drugs including an image of a drug having identification information stamped or printed on the surface thereof, on the basis of prescription information;
a collation image acquisition step of acquiring an image of a drug to be collated as a collation image;
a similarity calculation step of calculating similarities between partial images in each corresponding divided region among a plurality of divided regions of the registered image acquired in the registered image acquisition step and a plurality of divided regions of the collation image acquired in the collation image acquisition step; and
a determination step of determining whether the drug indicated by the registered image and the drug indicated by the collation image are the same type, on the basis of the lowest similarity among a plurality of similarities calculated in the similarity calculation step; and
wherein the similarity calculation unit calculates the similarity using a correlation operation between the partial image of the registered image acquired by the registered image acquisition unit and the partial image of the collation image acquired by the collation image acquisition unit, and wherein the determination process unit uses the lowest similarity value as a basis of comparison with a threshold value.

18. A drug collation method executed by the at least one processor according to claim 17, further comprising:
a partial image extraction step of extracting, as partial images, images in regions corresponding to feature regions, in which there is a difference between the identification information of the drug based on the prescription information and the identification information of a drug that is similar to the drug based on the prescription information, from the registered image acquired in the registered image acquisition step and the collation image acquired in the collation image acquisition step; and
the similarity calculation step of further calculates a similarity between the partial image of the registered image and the partial image of the collation image extracted in the partial image extraction step; and
the determination step of determining whether the drug indicated by the registered image and the drug indicated by the collation image are the same type, on the basis of the similarity calculated in the similarity calculation step.

19. A drug collation device comprising at least one processor having:
- a registered image acquisition process unit that acquires an image of a drug as a registered image from an image storage unit which stores images of a plurality of types of drugs including an image of a drug having identification information stamped or printed on the surface thereof, on the basis of prescription information;
- a collation image acquisition process unit that acquires, as a collation image, an image of a drug to be collated with the registered image acquired by the registered image acquisition process unit;
- a similarity calculation process unit that calculates similarities between partial images in each corresponding divided region among a plurality of divided regions of the registered image acquired by the registered image acquisition process unit and a plurality of divided regions of the collation image acquired by the collation image acquisition process unit; and
- a determination process unit that determines whether the drug indicated by the registered image and the drug indicated by the collation image are the same type, on the basis of the lowest similarity among a plurality of similarities which are calculated for each of the plurality of divided region by the similarity calculation process unit, wherein the similarity calculation process unit calculates similarities between partial images with respect to an upper right side, lower right side, upper left side and lower left side of the registered image and the collation image, and wherein the determination process unit determines whether the drug indicated by the registered image and the drug indicated by the collation image are the same type on the basis of the lowest similarity among the upper right side, lower right side, upper left side and lower left side for the registered image and the collation image, and a comparison of the lowest similarity with respect to a predetermined threshold.

* * * * *